(12) United States Patent
Faust et al.

(10) Patent No.: US 7,699,807 B2
(45) Date of Patent: Apr. 20, 2010

(54) DEVICE AND METHOD FOR INSERTION OF A CANNULA OF AN INFUSION DEVICE

(75) Inventors: Mark Faust, Lino Lakes, MN (US); James Marrs, Arden Hills, MN (US); Steve Cote, Stillwater, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 1730 days.

(21) Appl. No.: 10/705,725

(22) Filed: Nov. 10, 2003

(65) Prior Publication Data

US 2005/0101912 A1    May 12, 2005

(51) Int. Cl.
*A61M 5/20* (2006.01)
(52) U.S. Cl. .................................... 604/157
(58) Field of Classification Search ........... 604/164.01, 604/164.07, 164.08, 110, 192, 195, 111, 604/136, 131, 157
See application file for complete search history.

(56) References Cited

U.S. PATENT DOCUMENTS

| | | | |
|---|---|---|---|
| 3,547,119 A | 12/1970 | Hall et al. | |
| 4,531,937 A | 7/1985 | Yates | |
| 4,755,173 A | 7/1988 | Konopka et al. | |
| 4,805,791 A * | 2/1989 | Begley | 215/252 |
| 4,994,042 A | 2/1991 | Vadher | |
| 5,092,853 A | 3/1992 | Couvertier, II | |
| 5,129,884 A | 7/1992 | Dysarz | |
| 5,135,496 A * | 8/1992 | Vetter et al. | 604/111 |
| 5,137,516 A | 8/1992 | Rand et al. | |
| 5,176,650 A | 1/1993 | Haining | |
| 5,176,662 A | 1/1993 | Bartholomew et al. | |
| 5,257,980 A | 11/1993 | Van Antwerp et al. | |
| 5,451,210 A | 9/1995 | Kramer et al. | |
| 5,522,803 A | 6/1996 | Teissen-Simony | |
| 5,545,143 A | 8/1996 | Fischell | |
| 5,573,510 A | 11/1996 | Isaacson | |
| 5,575,777 A | 11/1996 | Cover et al. | |
| 5,584,813 A | 12/1996 | Livingston et al. | |
| 5,591,188 A | 1/1997 | Waisman | |
| 5,676,156 A | 10/1997 | Yoon | |

(Continued)

FOREIGN PATENT DOCUMENTS

DE    299 05 072 U1    9/1999

(Continued)

*Primary Examiner*—Nicholas D Lucchesi
*Assistant Examiner*—Christopher D Koharski
(74) *Attorney, Agent, or Firm*—Merchant & Gould P.C.

(57) ABSTRACT

A device for inserting a cannula of a subcutaneous infusion device into a subcutaneous layer of skin of a patient. For example, some devices automatically retract a needle used to introduce the cannula of a subcutaneous infusion device into the subcutaneous layer of skin of a patient. The device can include a housing with an internal cavity, as well as a needle coupled to the housing. The needle can be coupled to a cannula of a subcutaneous infusion device. A member can move the needle. Upon full introduction of the needle and associated cannula of the subcutaneous infusion device into a subcutaneous layer of skin of a patient, the member is automatically actuated to move the needle into the internal cavity of the housing into the retracted state while leaving the cannula of the subcutaneous infusion device in the subcutaneous layer of skin of the patient.

18 Claims, 30 Drawing Sheets

U.S. PATENT DOCUMENTS

| | | |
|---|---|---|
| 5,738,641 A | 4/1998 | Watson |
| 5,817,058 A | 10/1998 | Shaw |
| 5,833,666 A | 11/1998 | Davis |
| 5,848,990 A | 12/1998 | Cirelli et al. |
| 5,851,197 A | 12/1998 | Marano et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,056,726 A | 5/2000 | Isaacson |
| 6,077,244 A | 6/2000 | Botich et al. |
| 6,086,575 A | 7/2000 | Mejslov |
| 6,093,172 A | 7/2000 | Funderburk et al. |
| 6,123,690 A | 9/2000 | Mejslov |
| 6,159,181 A | 12/2000 | Crossman et al. |
| 6,293,925 B1 | 9/2001 | Safabash et al. |
| 6,302,866 B1 | 10/2001 | Marggi |
| 6,355,021 B1 | 3/2002 | Nielsen et al. |
| 6,450,992 B1 | 9/2002 | Cassidy, Jr. |
| 6,520,938 B1 | 2/2003 | Funderburk et al. |
| 6,572,586 B1 | 6/2003 | Wojcik |
| 6,579,267 B2 | 6/2003 | Lynch et al. |
| 6,607,509 B2 | 8/2003 | Bobroff et al. |
| 6,620,136 B1 | 9/2003 | Pressly, Sr. et al. |
| 6,685,674 B2 | 2/2004 | Douglas et al. |
| 6,736,797 B1 | 5/2004 | Larsen et al. |
| 6,830,562 B2 * | 12/2004 | Mogensen et al. ..... 604/164.12 |
| 6,926,694 B2 * | 8/2005 | Marano-Ford et al. . 604/167.05 |
| 7,018,344 B2 | 3/2006 | Bressler et al. |
| 7,052,483 B2 | 5/2006 | Wojcik |
| 7,056,302 B2 | 6/2006 | Douglas |
| 2001/0053889 A1 | 12/2001 | Marggi et al. |
| 2002/0045867 A1 | 4/2002 | Nielsen et al. |
| 2002/0077599 A1 | 6/2002 | Wojcik |
| 2002/0161332 A1 | 10/2002 | Ramey |
| 2002/0173769 A1 | 11/2002 | Gray et al. |
| 2003/0014018 A1 | 1/2003 | Giambattista et al. |
| 2003/0060781 A1 | 3/2003 | Mogensen et al. |
| 2003/0109829 A1 | 6/2003 | Mogensen et al. |
| 2003/0125669 A1 | 7/2003 | Safabash et al. |
| 2003/0130619 A1 | 7/2003 | Safabash et al. |
| 2003/0158520 A1 | 8/2003 | Safabash et al. |
| 2003/0199823 A1 | 10/2003 | Bobroff et al. |
| 2003/0225373 A1 | 12/2003 | Bobroff et al. |
| 2003/0225374 A1 | 12/2003 | Mathiasen |
| 2004/0002682 A1 | 1/2004 | Kovelman et al. |
| 2004/0143216 A1 | 7/2004 | Douglas et al. |
| 2004/0158207 A1 * | 8/2004 | Hunn et al. ............ 604/164.01 |
| 2004/0199123 A1 | 10/2004 | Nielsen |
| 2004/0204687 A1 | 10/2004 | Mogensen et al. |
| 2004/0215151 A1 | 10/2004 | Marshall et al. |
| 2004/0236284 A1 | 11/2004 | Hoste et al. |
| 2004/0260250 A1 | 12/2004 | Harris et al. |
| 2005/0043687 A1 | 2/2005 | Mogensen et al. |
| 2005/0075606 A1 | 4/2005 | Botich et al. |
| 2005/0101933 A1 | 5/2005 | Marrs |
| 2005/0107743 A1 | 5/2005 | Fangrow |
| 2005/0131346 A1 | 6/2005 | Douglas |
| 2006/0041224 A1 | 2/2006 | Jensen |
| 2006/0173413 A1 | 8/2006 | Fan |

FOREIGN PATENT DOCUMENTS

| | | |
|---|---|---|
| DE | 202 20 543 U1 | 10/2003 |
| EP | 0 290 176 A1 | 11/1988 |
| EP | 0 239 244 B1 | 9/1991 |
| EP | 0 451 040 A1 | 10/1991 |
| EP | 0 615 768 B1 | 12/1999 |
| WO | WO 96/32981 | 10/1996 |
| WO | WO 02/081012 A2 | 10/2002 |
| WO | WO 02/102442 A1 | 12/2002 |

* cited by examiner

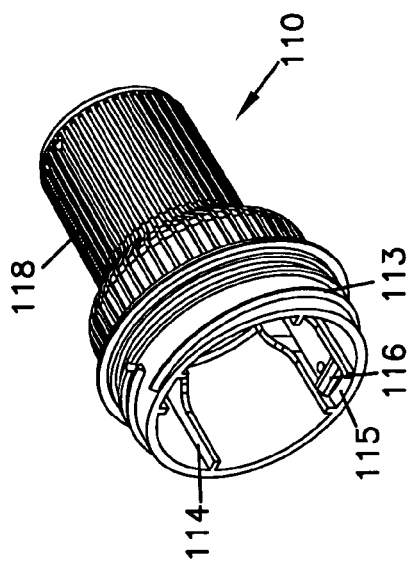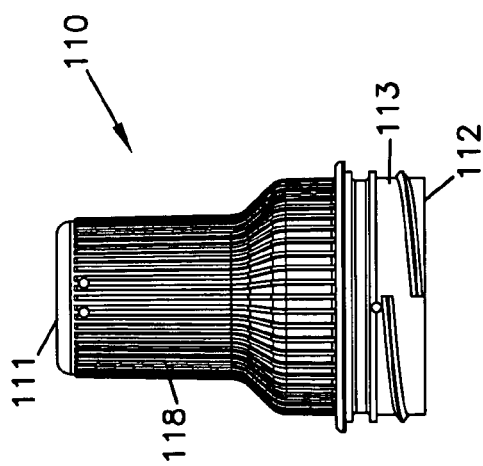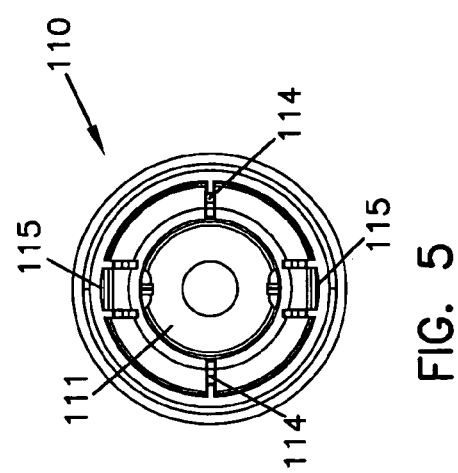

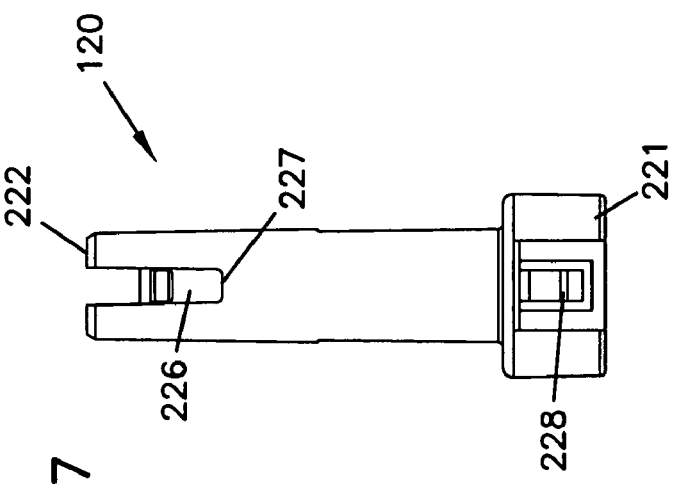
FIG. 6
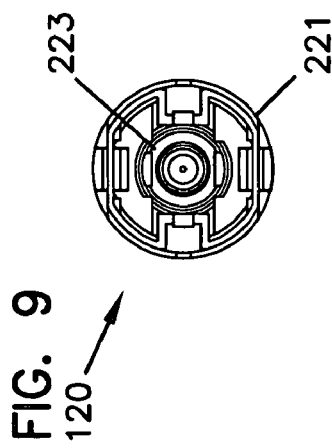
FIG. 7
FIG. 9
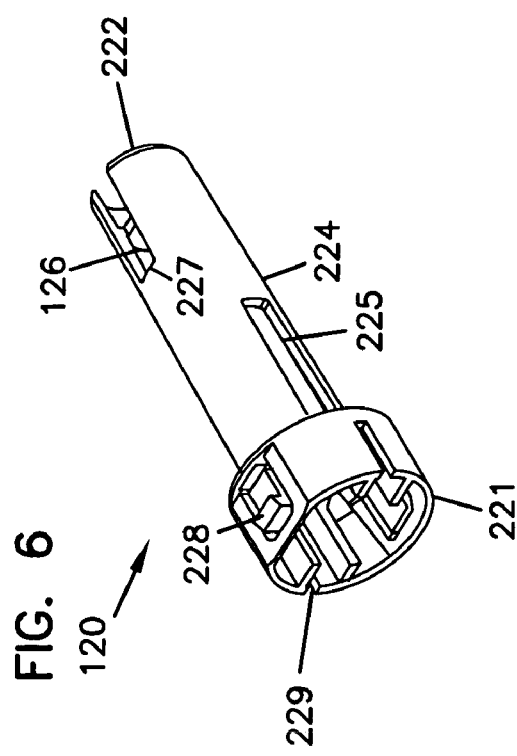
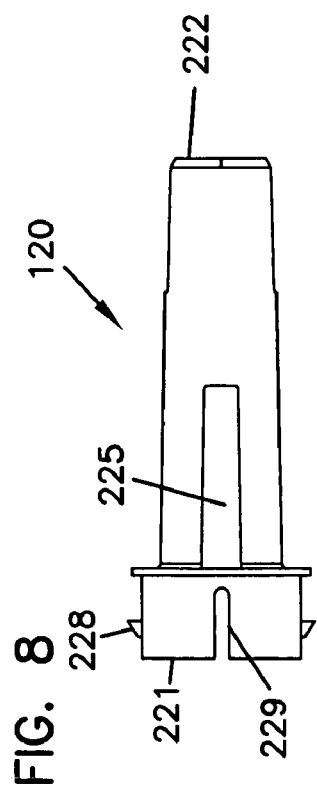
FIG. 8

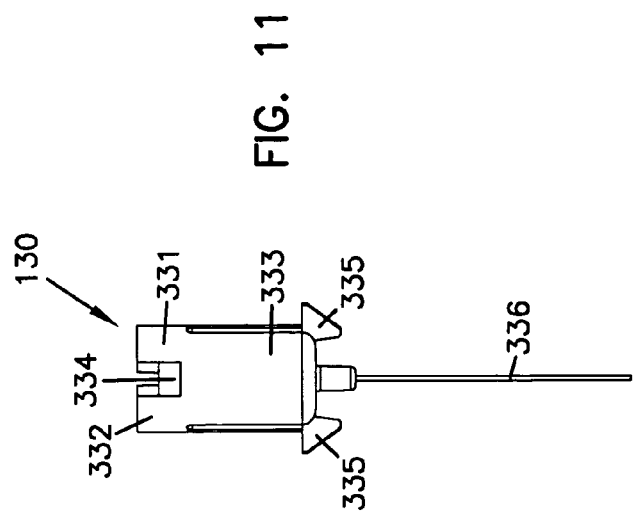
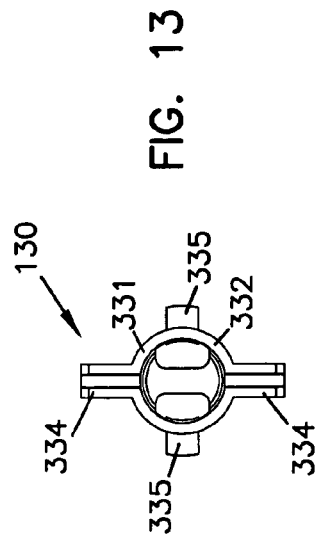
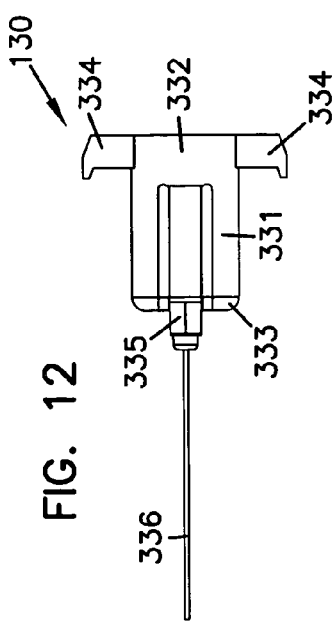
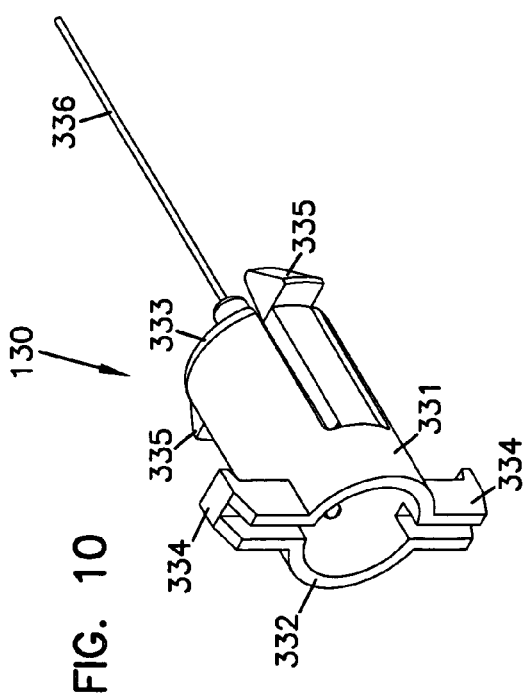

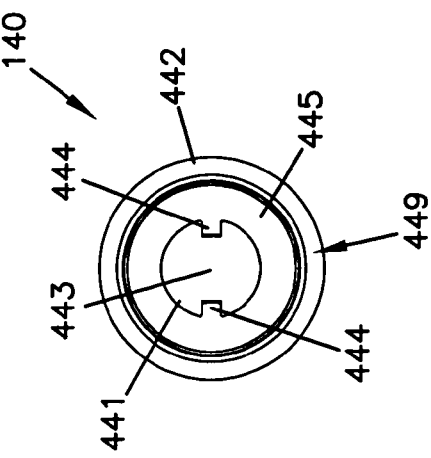
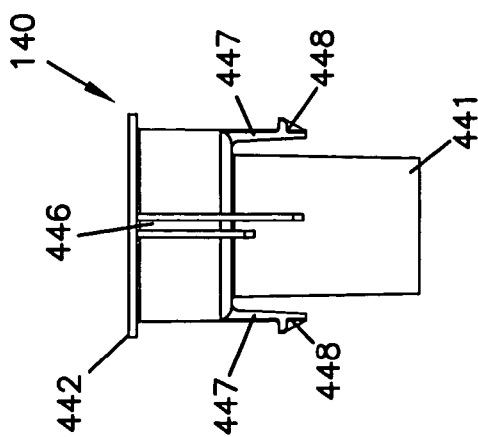
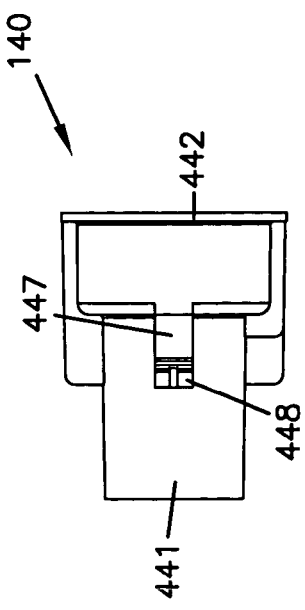
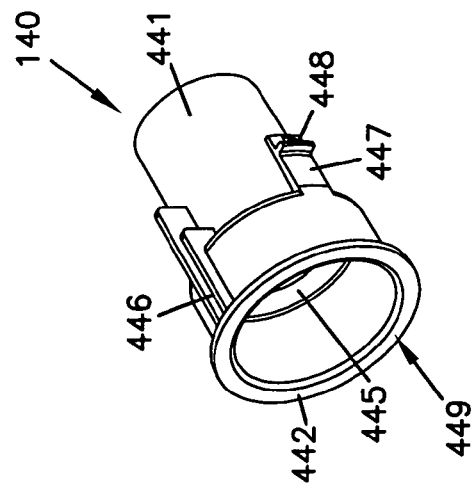

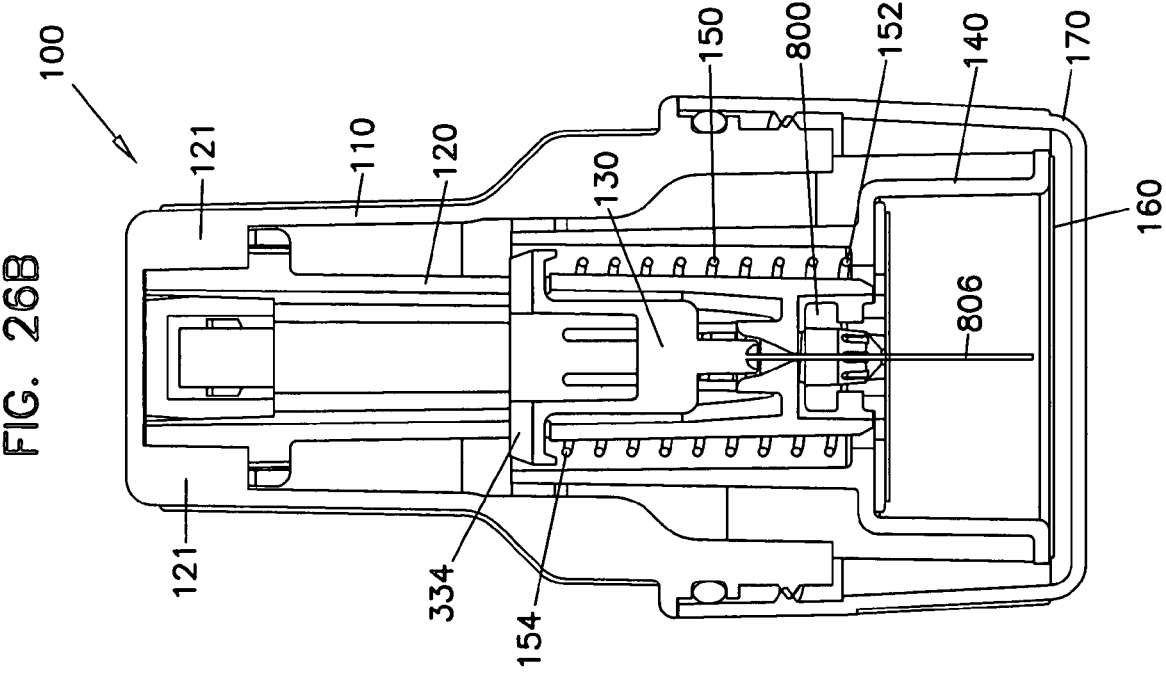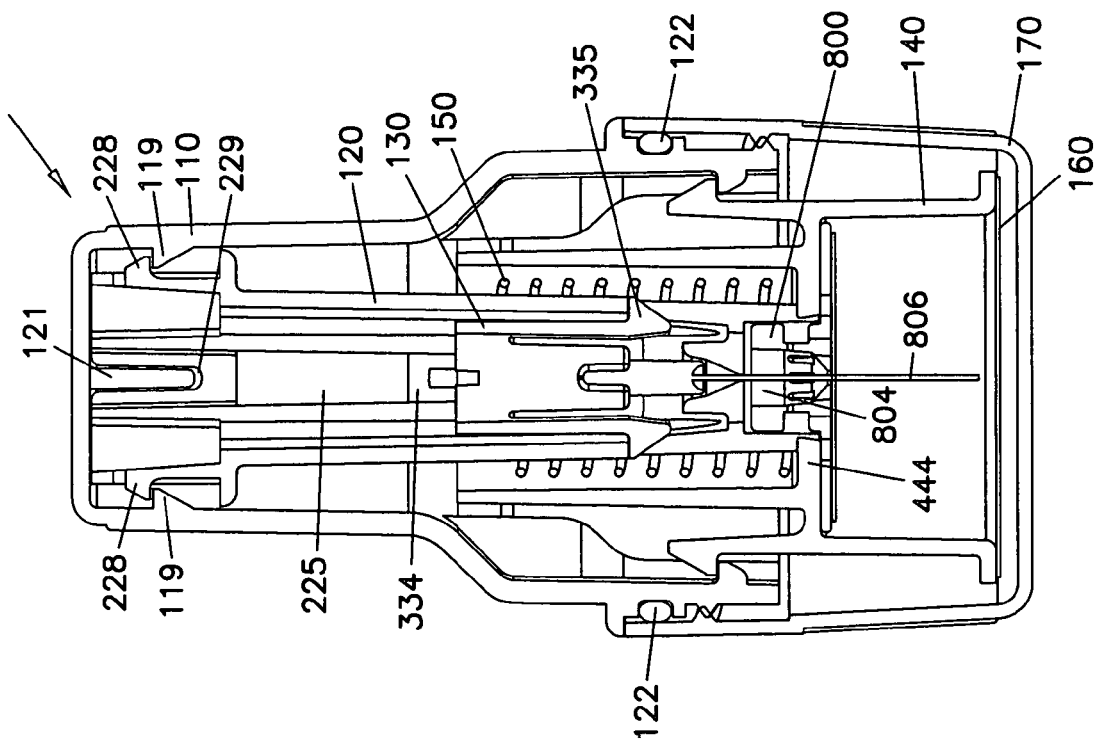

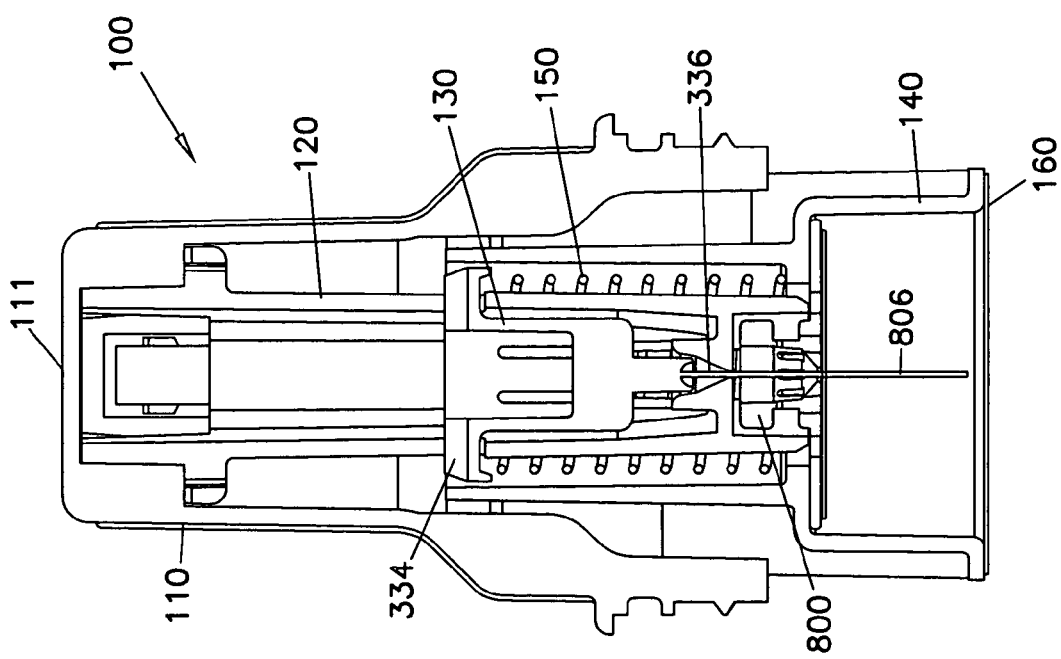
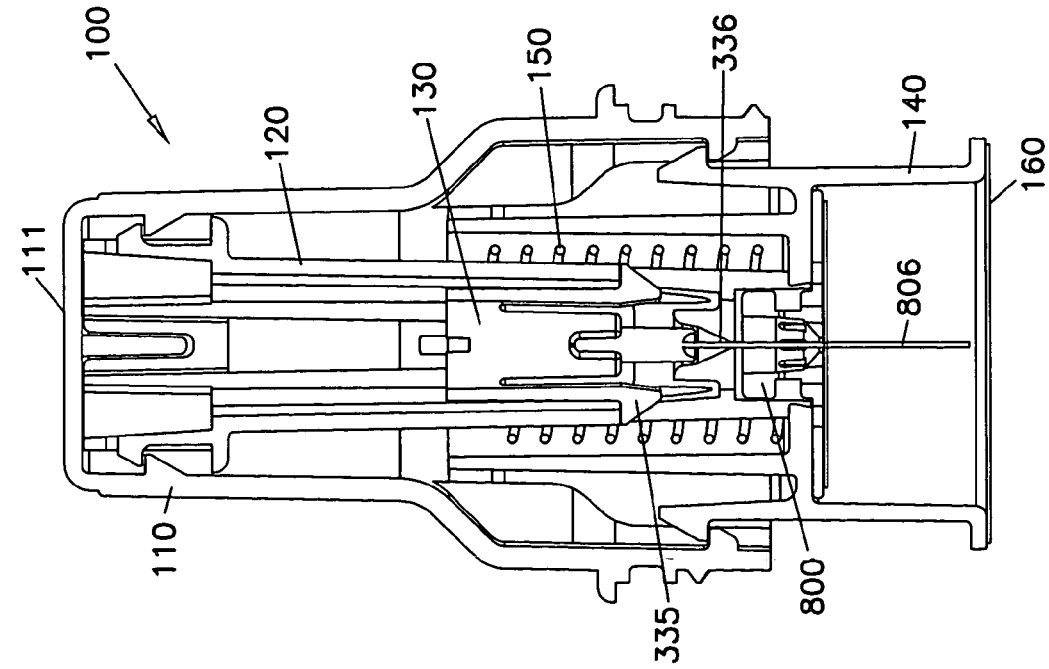

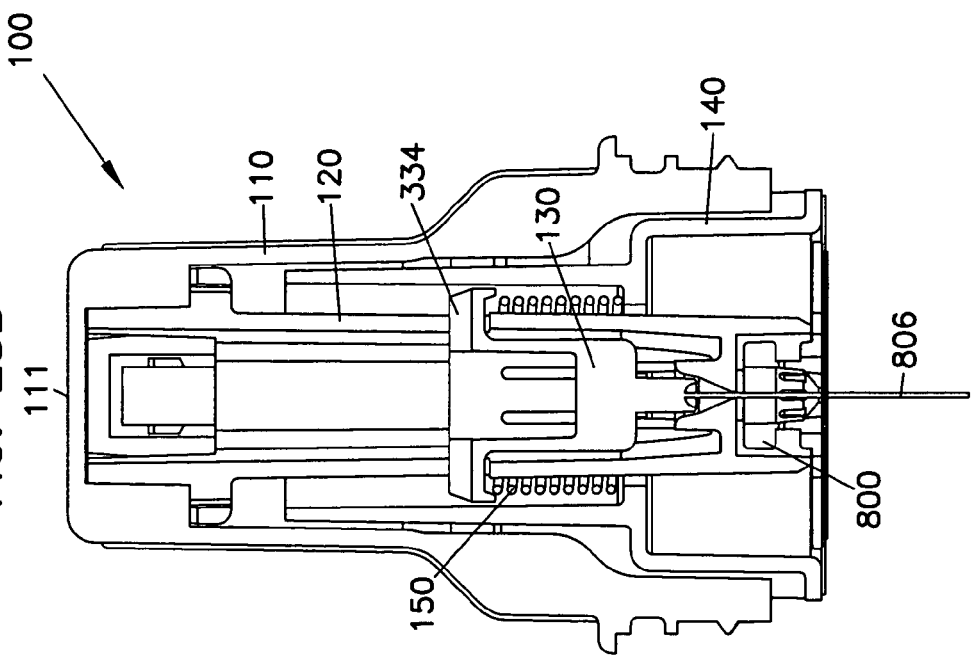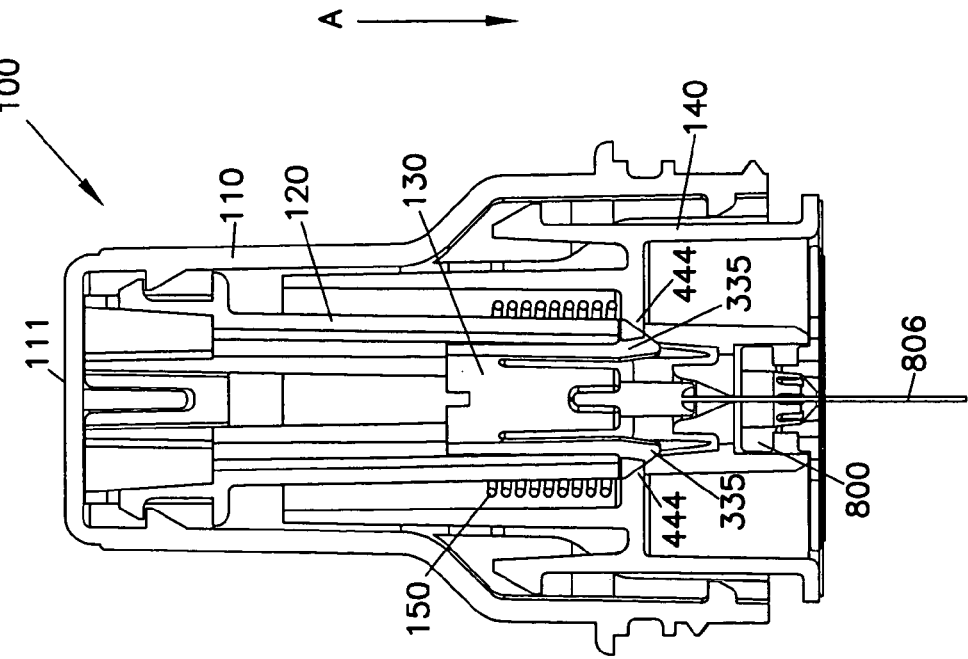

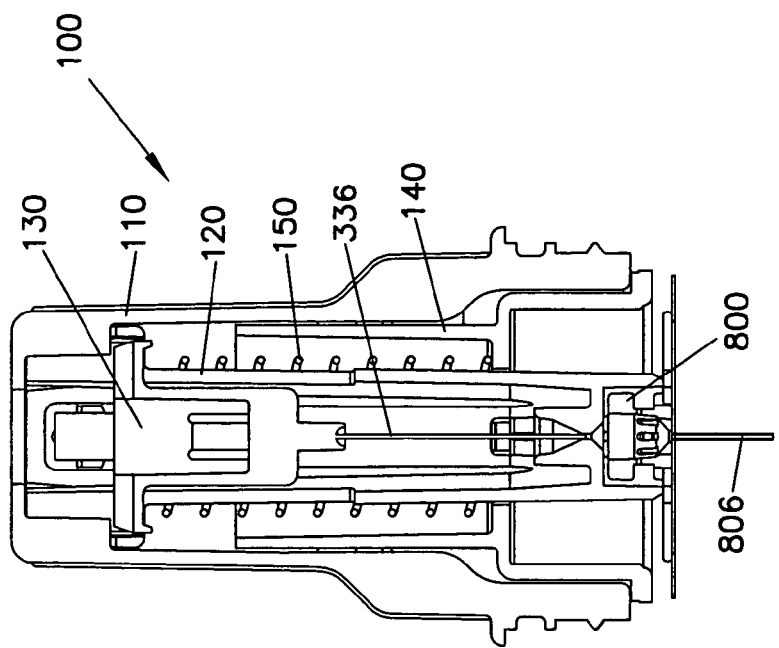
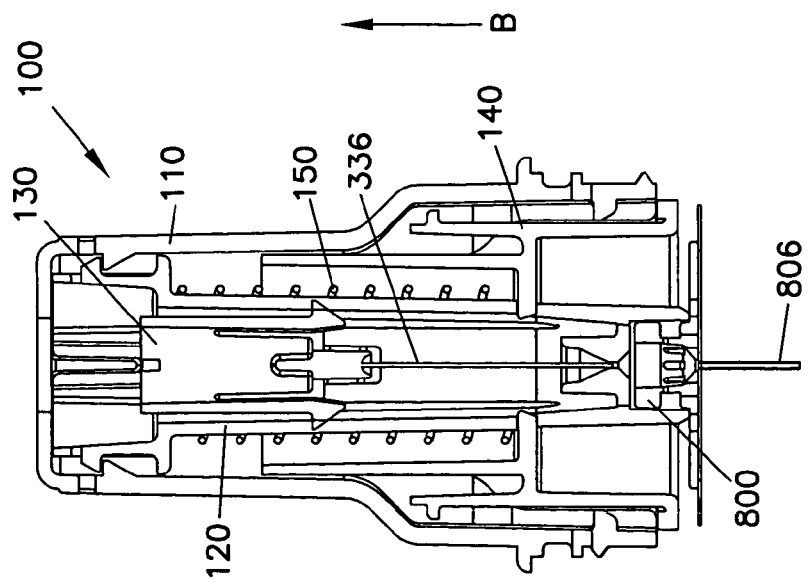
FIG. 29A
FIG. 29B

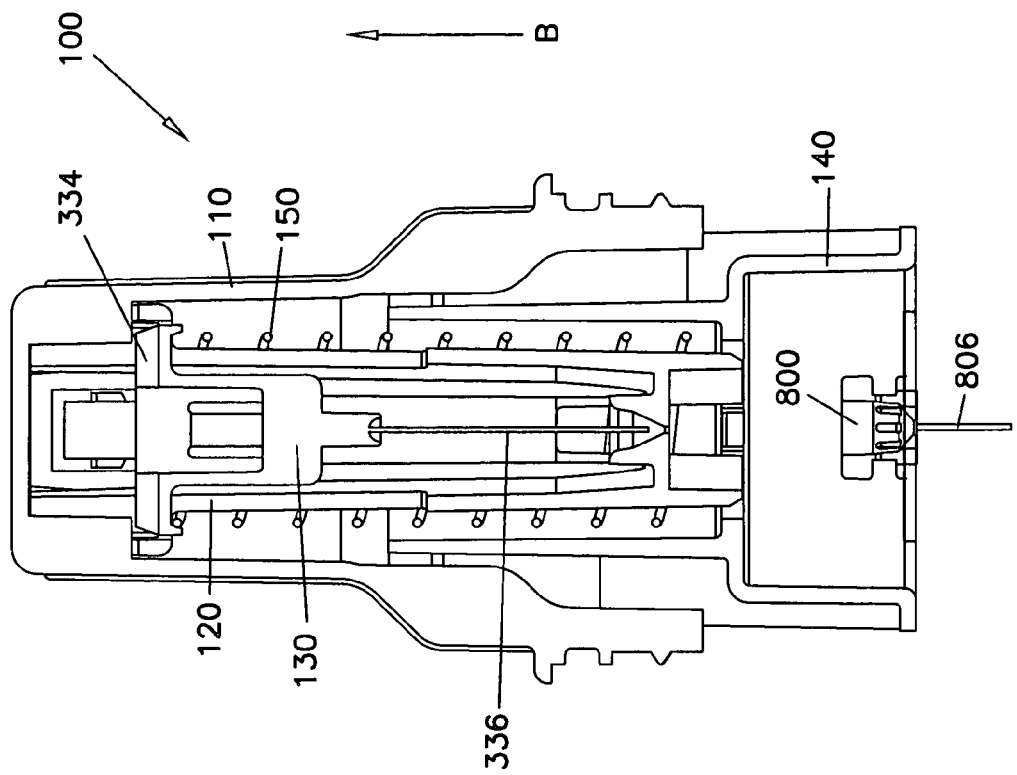
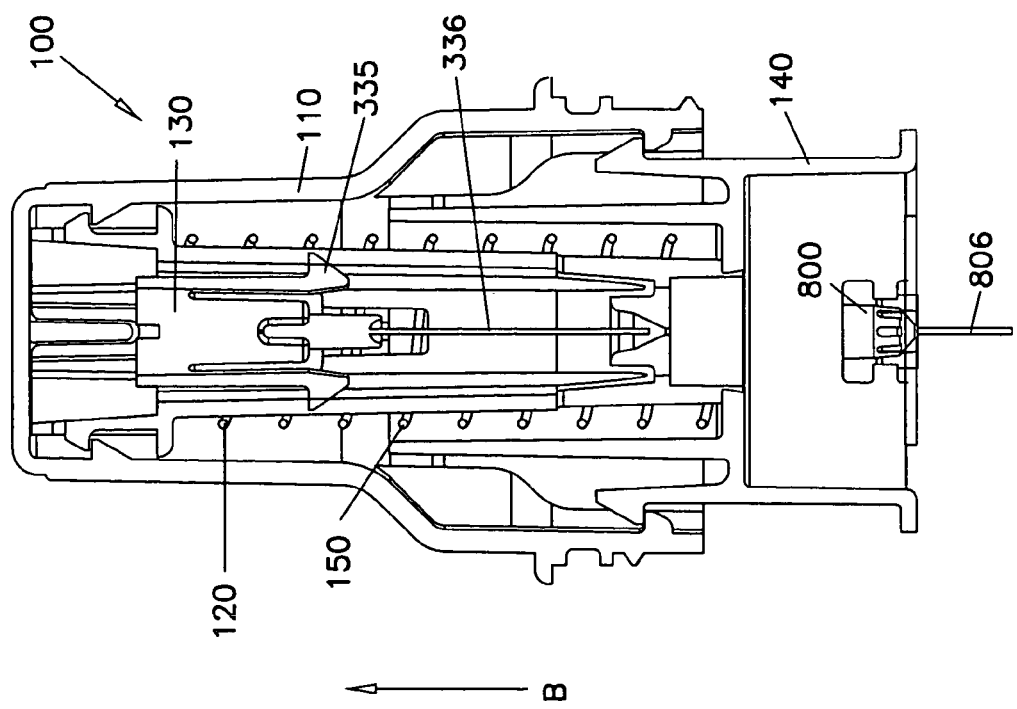

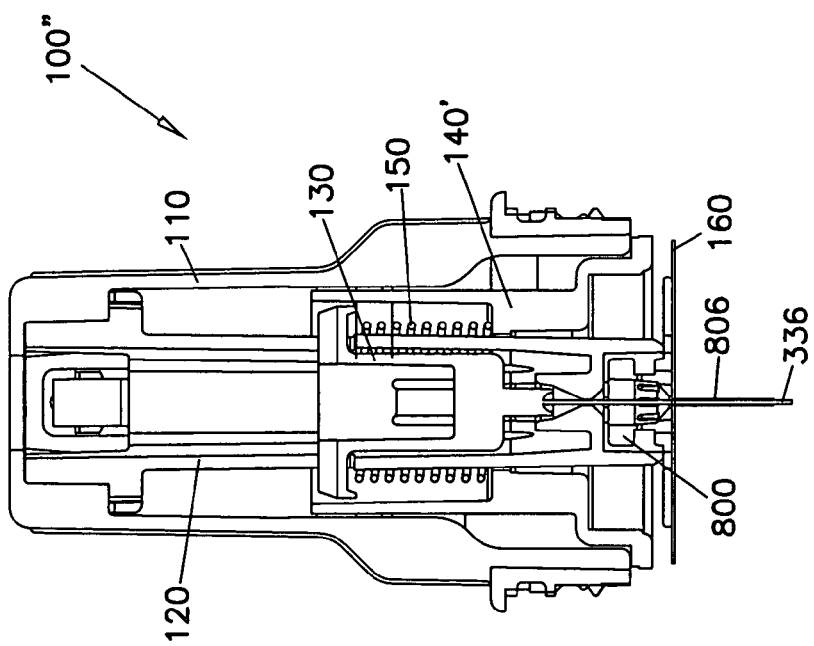
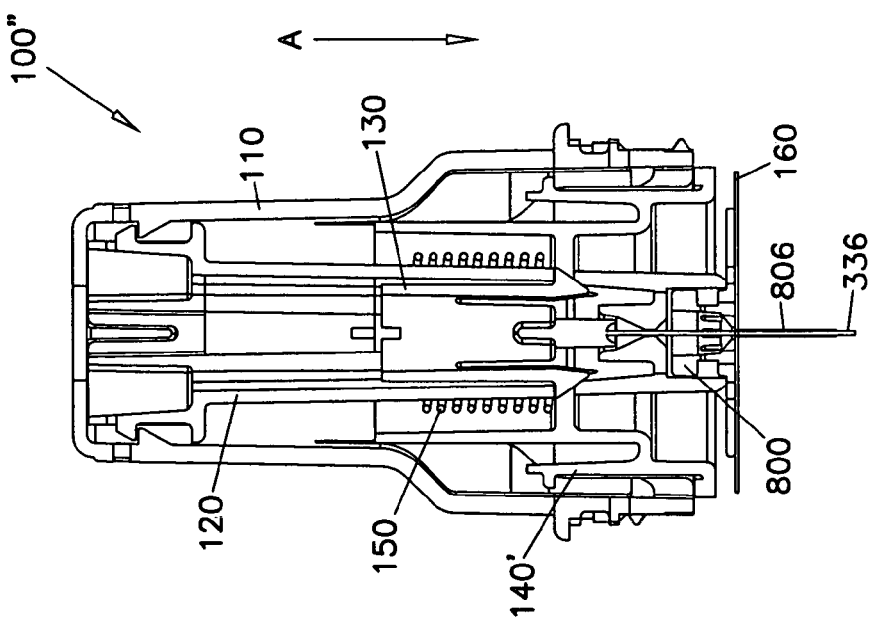

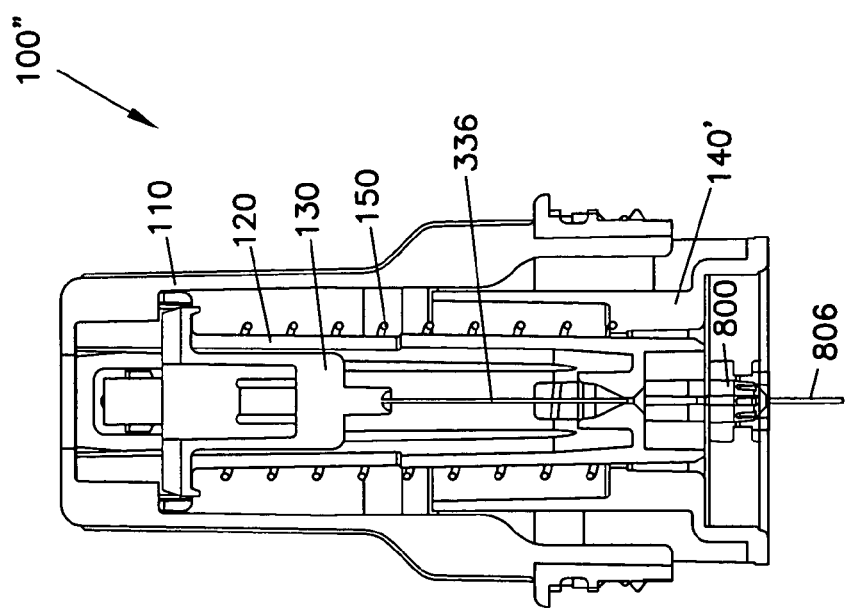
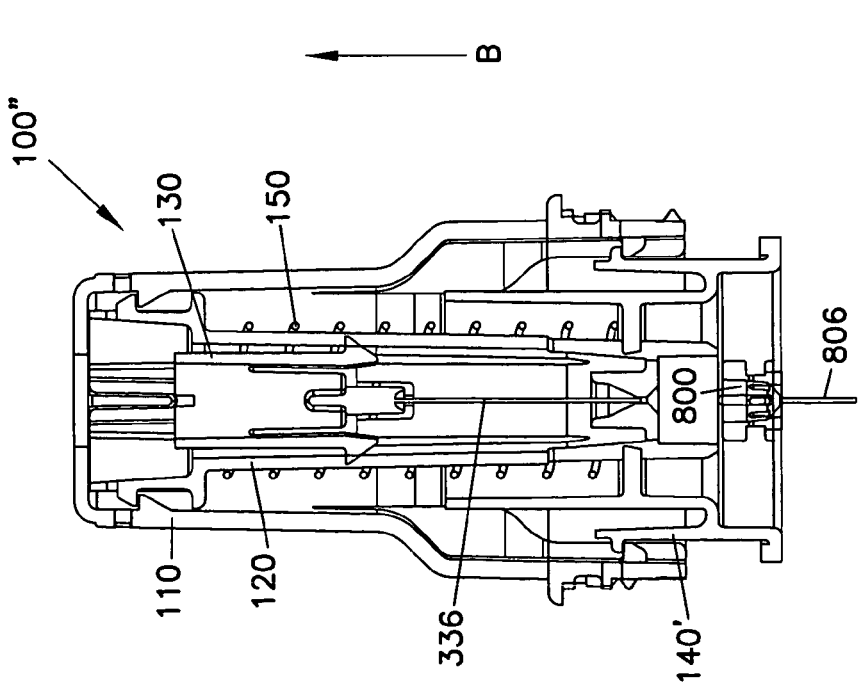

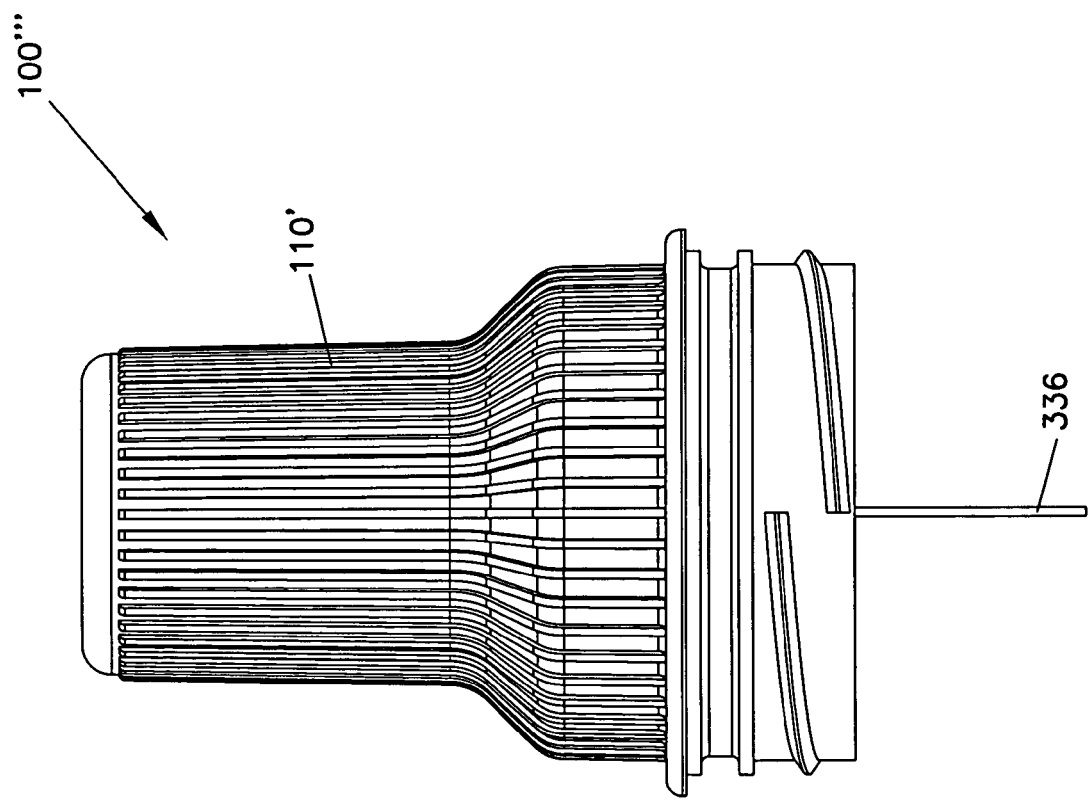

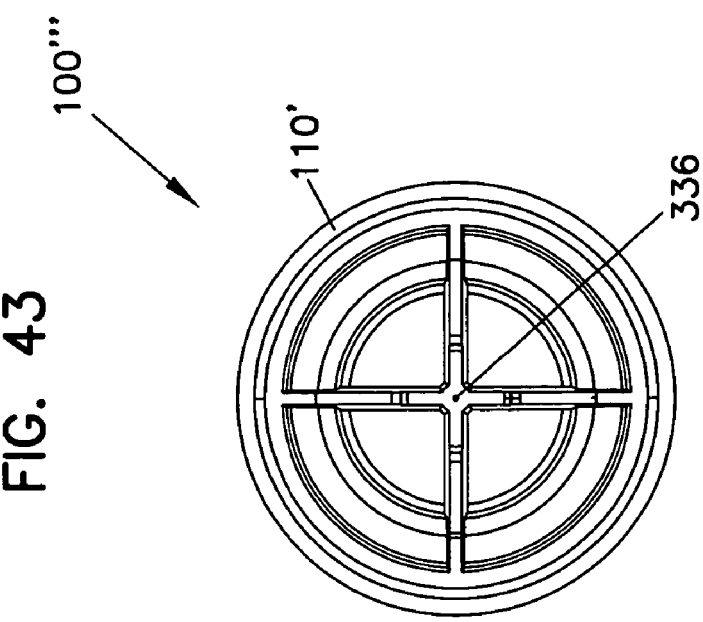
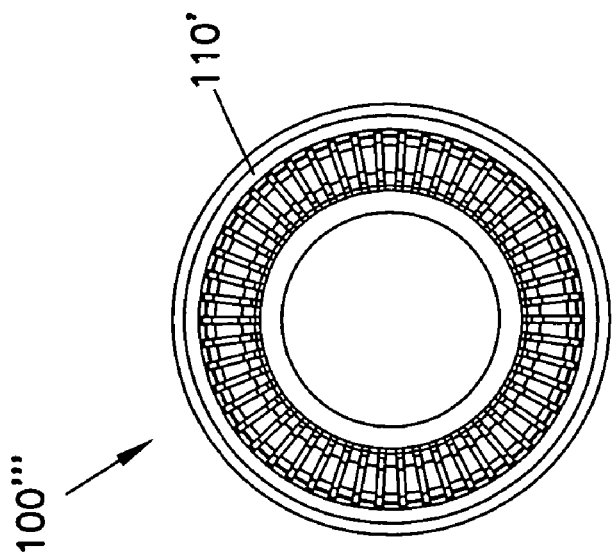

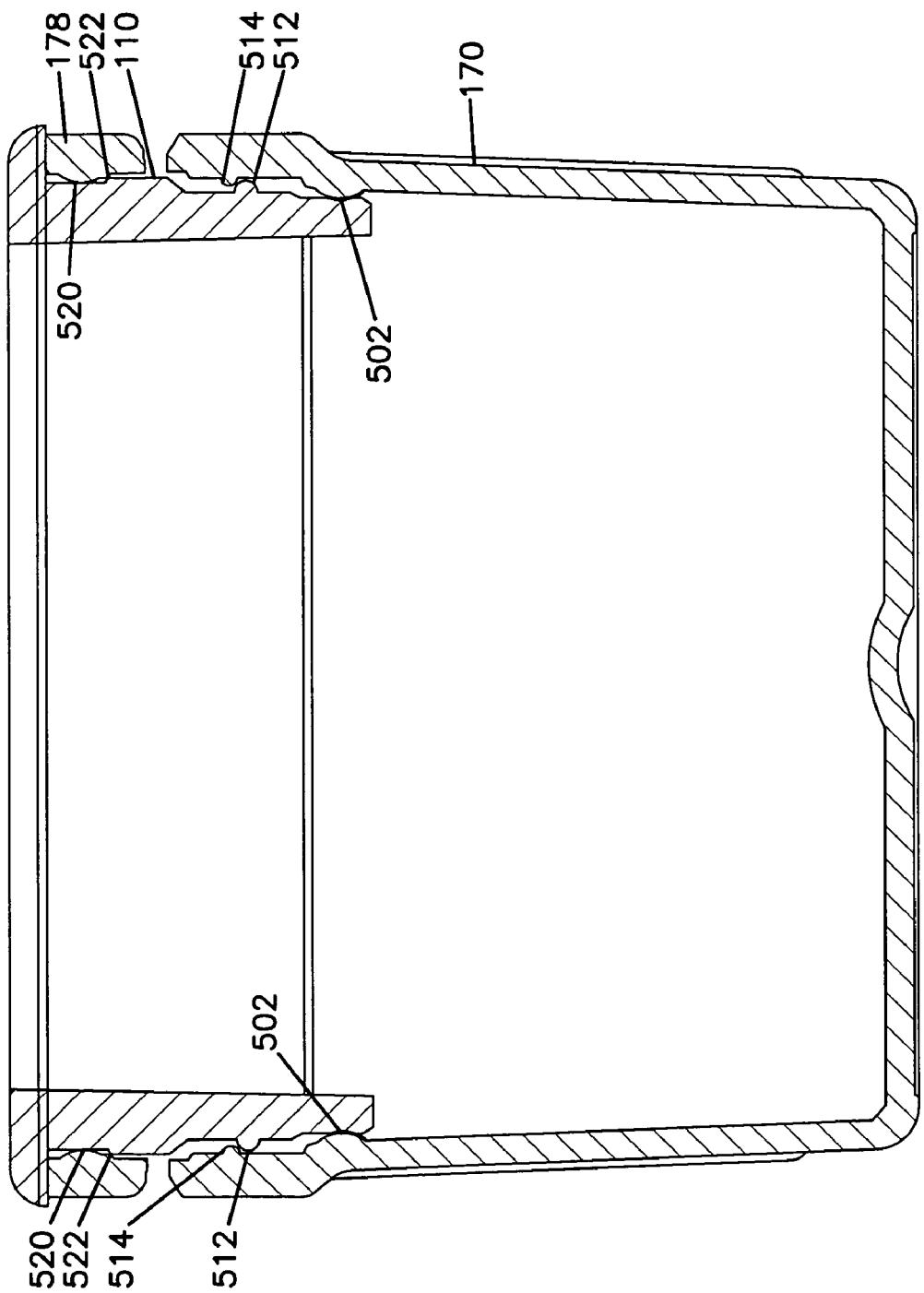

DEVICE AND METHOD FOR INSERTION OF A CANNULA OF AN INFUSION DEVICE

TECHNICAL FIELD

The present invention relates to a device for assisting in the introduction of a cannula of an infusion device into the skin of a patient for delivery of a substance to the patient.

BACKGROUND

Infusion devices are used to deliver substances such as medications into the subcutaneous layer of skin of a patient. Devices for assisting in insertion of the cannula of an infusion device into the skin of the patient are known. For example, some devices utilize springs to automatically drive a needle into the skin of a patient to introduce the cannula of the infusion device into the subcutaneous layer.

Because a needle is used to introduce the cannula of the infusion device into the subcutaneous layer of skin, there is a risk associated with inadvertent exposure to the needle. Further, patients may react adversely to viewing the needle prior to insertion and may, for example, be reluctant to place the needle into the skin. Prior devices may not adequately shroud this needle prior to and/or after introduction of the infusion device.

Other issues of concern in the design and use of insertion devices include ease of use by the patient and sterilization. For example, some patients may have difficulty loading the infusion device into the insertion device.

It is therefore desirable to provide new designs for devices used to assist in the introduction of an infusion device into the skin of a patient.

SUMMARY

Embodiments made in accordance with the present invention include devices that can be used to assist in the introduction of the cannula of an infusion device into the skin of a patient for delivery of a substance to the patient.

For example, one embodiment of a device includes a needle used to insert the cannula of an infusion device into the skin of a patient. Once the cannula of the infusion device is inserted into the skin, the device moves the needle to a retracted state within the device.

In another embodiment, a device is configured to move a needle and associated cannula of an infusion device from a delivery state to a trigger state at which the cannula of the infusion device is inserted into the skin of a patient. Upon full insertion of the cannula at the trigger state, the device is then configured to move the needle to a retracted state within the device.

In another embodiment, a device includes a needle that can be used to insert a cannula of a site into the skin of a patient. Upon insertion of the cannula, the needle can be removed from the skin. In one embodiment, a cap is provided that can be placed onto the device prior to and after use of the device to provide a sterile environment and/or to reduce exposure to the needle.

The above summary of the present invention is not intended to describe each disclosed embodiment or every implementation of the present invention. Figures in the detailed description that follow more particularly exemplify embodiments of the invention. While certain embodiments will be illustrated and described, the invention is not limited to use in such embodiments.

DESCRIPTION OF THE DRAWINGS

FIG. 3 is a perspective view of a housing of the device of FIG. 1.

FIG. 4 is a side view of the housing of FIG. 3.

FIG. 5 is an end view of the housing of FIG. 3.

FIG. 6 is a perspective view of a cylinder hub of the device of FIG. 1.

FIG. 7 is side view of the cylinder hub of FIG. 6.

FIG. 8 is another side view of the cylinder hub of FIG. 6.

FIG. 9 is an end view of the cylinder hub of FIG. 6.

FIG. 10 is a perspective view of a needle hub of the device of FIG. 1.

FIG. 11 is a side view of the needle hub of FIG. 10.

FIG. 12 is another side view of the needle hub of FIG. 10.

FIG. 13 is an end view of the needle hub of FIG. 10.

FIG. 14 is a perspective view of a sleeve of the device of FIG. 1.

FIG. 15 is a side view of the sleeve of FIG. 14.

FIG. 16 is another side view of the sleeve of FIG. 14.

FIG. 17 is an end view of the sleeve of FIG. 14.

FIG. 26A is a cross-sectional view taken along line 26A-26A of the device of FIG. 1 in a ship state.

FIG. 26B is a cross-sectional view taken along line 26B-26B of the device of FIG. 1 in the ship state.

FIG. 27A is a cross-sectional view taken along line 27A-27A of the device of FIG. 24 in a delivery state.

FIG. 27B is a cross-sectional view taken along line 27B-27B of the device of FIG. 24 in the delivery state.

FIG. 28A is a cross-sectional view taken along line 28A-28A of the device of FIG. 25 in a trigger state.

FIG. 28B is a cross-sectional view taken along line 28B-28B of the device of FIG. 25 in the trigger state.

FIG. 29A is a cross-sectional view of the device of FIG. 28A with the needle hub retracted.

FIG. 29B is a cross-sectional view of the device of FIG. 28B with the needle hub retracted.

FIG. 30A is a cross-sectional view taken along line 30A-30A of the device of FIG. 24 in a retracted state.

FIG. 30B is a cross-sectional view taken along line 30B-30B of the device of FIG. 24 in the retracted state.

FIG. 33A is a cross-sectional view of the device of FIG. 32A in a delivery state.

FIG. 33B is a cross-sectional view of the device of FIG. 32B in the delivery state.

FIG. 34A is a cross-sectional view of the device of FIG. 32A in a retracted state.

FIG. 34B is a cross-sectional view of the device of FIG. 32B in the retracted state.

FIG. 41 is a side view of the device of FIG. 39.

FIG. 42 is an end view of the device of FIG. 39.

FIG. 43 is an opposite end view of the device of FIG. 39.

FIG. 52 is a cross-sectional view taken along line 52-52 of a portion of the device of FIG. 50.

DETAILED DESCRIPTION

Embodiments of the present invention relate to devices for assisting in the introduction of an infusion device, specifically a cannula of the infusion device, into the subcutaneous layer of skin of a patient.

Figure 1:
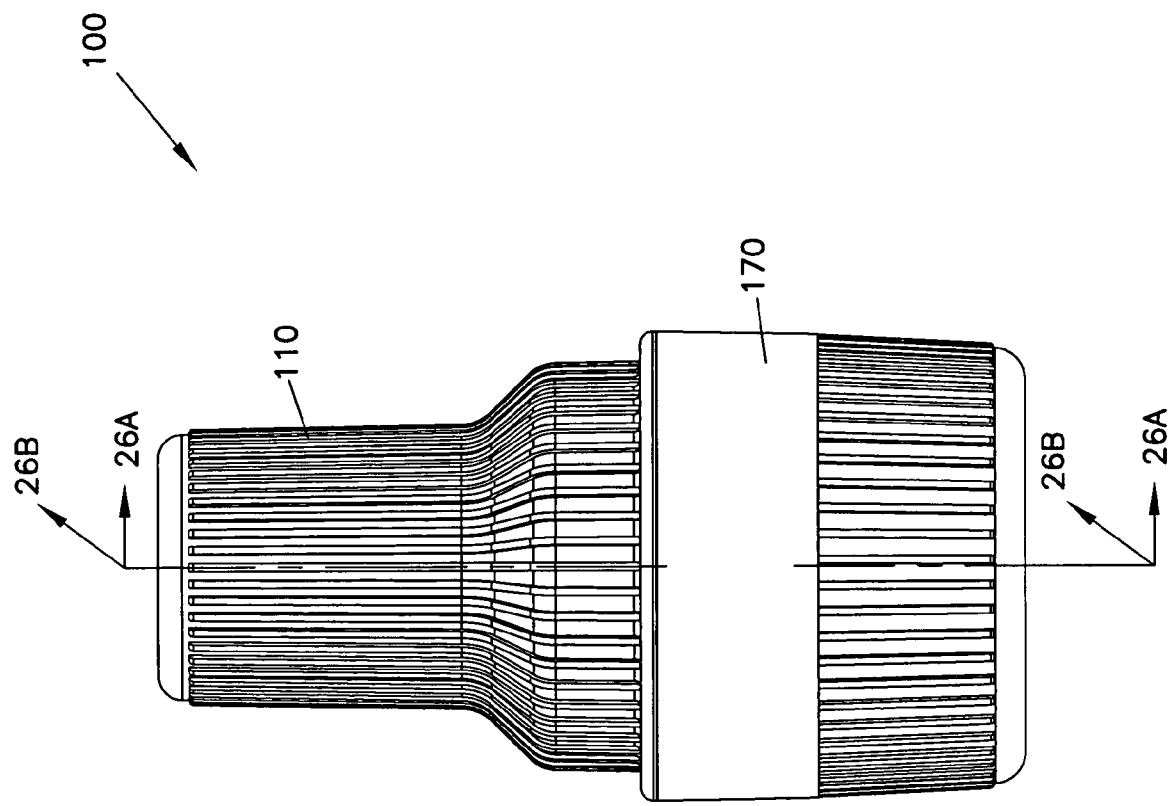
FIG. 1 is a side view of an example embodiment of a device used to introduce a cannula of an infusion device into a patient made in accordance with the present invention.
Figure 2:
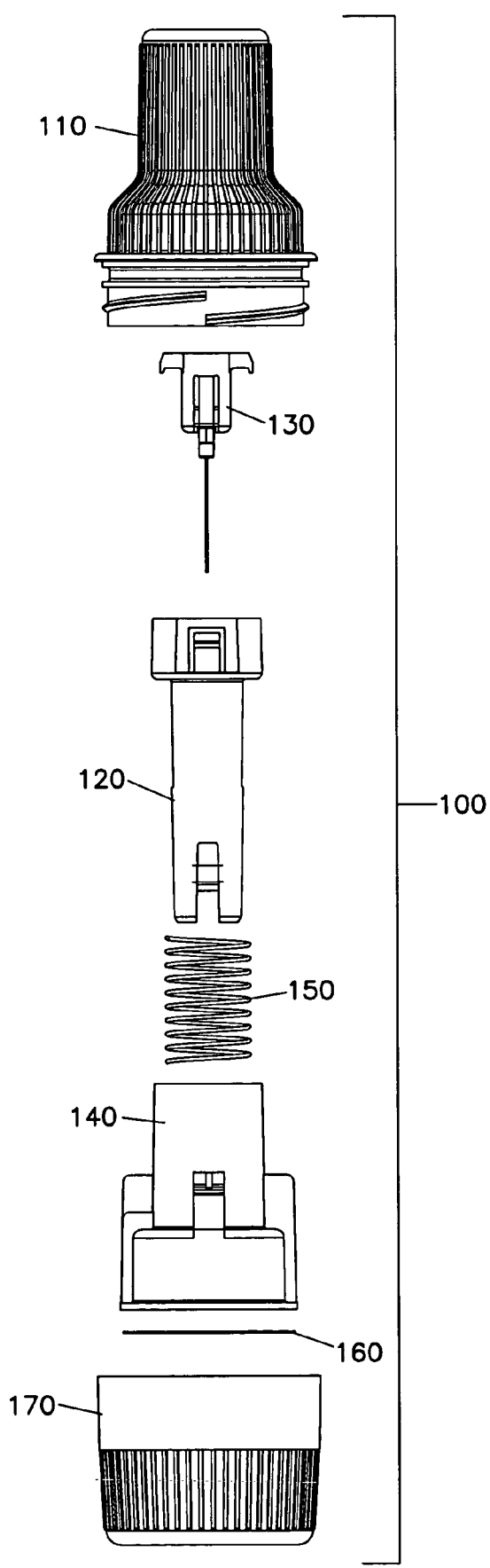
FIG. 2 is an exploded side view of the device of FIG. 1.

Referring to FIGS. 1 and 2, one example embodiment of a device 100 is shown. The device 100 is used to introduce a cannula of an infusion device, such as a set, site, or other access device, into the skin of the patient. The set, site, or other access device can then be used to deliver drugs or other fluid to the patient, such as from an infusion pump.

The device 100 generally includes a housing 110, a cylinder hub 120, a needle hub 130, a sleeve 140, a spring 150, an adhesive portion 160, and a cap 170. Each of the components of the device 100, described further below, is configured to assist in the introduction of a cannula of an infusion device into the skin of a patient.

Referring now to FIGS. 3-5, the housing 110 is shown. The housing 110 is preferably cylindrical in shape and includes a closed upper end 111 and an open lower end 112. The housing 110 further preferably includes a portion 118 with a knurled surface to enhance a patient's grip on the housing 110, as well as a threaded portion 113 positioned adjacent the open lower end 112.

Referring now to FIGS. 6-9, the cylinder hub 120 is shown in greater detail. The cylinder hub 120 includes first and second ends 221 and 222 and an interior passage 223. In addition, two opposing slots 225 are formed on opposite sides of the cylinder hub 120 and generally extend from a midportion 224 of the hub 120 to the first end 221. Further, the cylinder hub 120 includes opposing apertures 226 formed in the cylinder hub 120 adjacent the second end 222.

The first end 221 of the cylinder hub 120 is coupled to the upper end 111 of the housing 110 by tabs 119 on the housing 110 engaging shoulders 228 formed by the cylinder hub 120. See, for example, FIGS. 6-8, 26A, and 26B. In addition, members 121 of the housing 110 are received in slots 229 of the cylinder hub 120. In alternative designs, the housing 110 and cylinder hub 120 can be formed as a single unit.

Referring now to FIGS. 10-13, the needle hub 130 includes a main body 331 with first and second ends 332 and 333, and a needle 336 (hollow or solid) coupled to the main body 331. The main body 331 includes opposing wings 334 formed at the first end 332 and opposing barbs 335 at the second end 333.

The needle hub 130 is positioned in the interior passage 223 of the cylinder hub 120 such that the opposing wings 334 of the needle hub 130 extend through the opposing slots 225 of the cylinder hub 120. See FIGS. 6, 8, 26B, 27B, 28B, 29B, and 30B. In addition, the opposing barbs 335 of the needle hub 130 extend through the opposing apertures 226 of the cylinder hub 120 and engage shoulders 227 formed by the apertures 226 so that the needle hub 130 is held in a fixed position relative to the cylinder hub 120 and the housing 110. See, for example, FIGS. 6, 8, 26A, 27A, and 28A.

Referring now to FIGS. 14-17, the sleeve 140 is shown. The sleeve 140 is preferably cylindrical in shape and includes first and second ends 441 and 442 and interior passage 443. Opposing projections 444 extend into the passage 443 adjacent to a shoulder 445. On the exterior of the sleeve 140 channels 446 are formed, as well as railways 447 with barbs 448 formed on ends thereof.

The sleeve 140 is coupled to the housing 110 such that the housing 110 can be moved longitudinally with respect to the sleeve 140. Specifically, the railways 114 of the housing are received in the channels 446 of the sleeve 140. Likewise, the railways 447 of the sleeve 140 are received in the channels 115 of the housing 110. Barbs 448 on the railways 447 of the sleeve 140 engage projections 116 in the channels 115 of the housing 110 so that the housing 110 remains slideably coupled to the sleeve 140 in opposition to the force exerted by the spring 150 (described further below).

The spring 150 includes first and second ends 152 and 154. See, for example, FIG. 26B. The spring 150 surrounds a portion of the cylinder hub 120 and extends within the passage 443 of the sleeve 140. The first end 152 of the spring 150 is seated on the shoulder 445 of the sleeve 140, and the second end 154 of the spring 150 engages the opposing wings 334 of the needle hub 130 extending through the opposing slots 225 of the cylinder hub 120.

The spring 150 is in a compressed state as shown in FIGS. 26A, 26B, 27A, 27B, 28A, and 28B and therefore applies force against the wings 334 of the needle hub 130, biasing the needle hub 130 in an upward direction. However, barbs 335 of the main body 331 of the needle hub 130 are engaged against shoulders 227 of the apertures 226 of the cylinder hub 120 to retain the needle hub 130 in place with respect to the cylinder hub 120. See, for example, FIG. 26A. Likewise, the spring 150 forces the housing 110 and the sleeve 140 apart until barbs 448 of the sleeve 140 engage projections 115 of the housing 110 to maintain coupling between the housing 110 and the sleeve 140.

Figure 18:
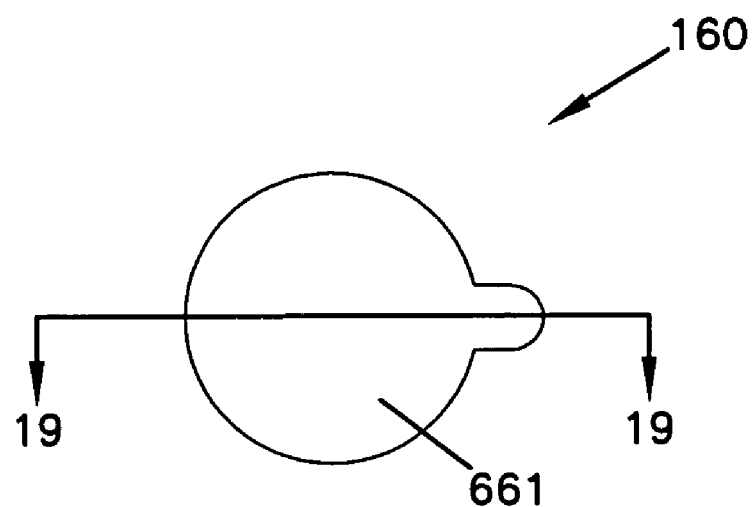
FIG. 18 is a top view of an adhesive portion of the device of FIG. 1.
Figure 19:
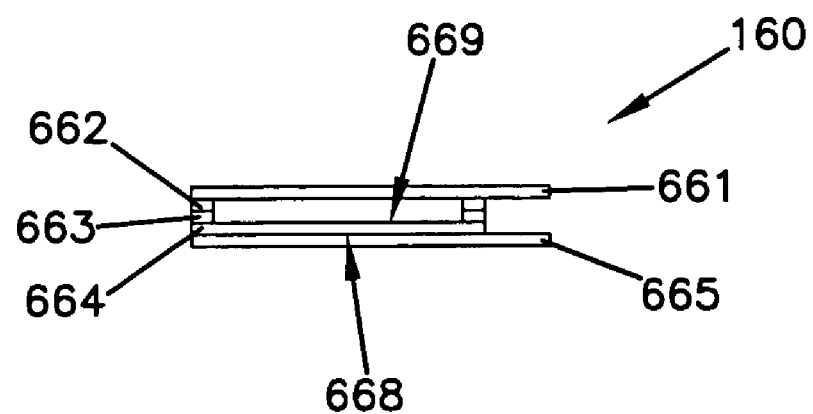
FIG. 19 is a cross-sectional view taken along line 19-19 of the adhesive portion of FIG. 18.
Figure 20:
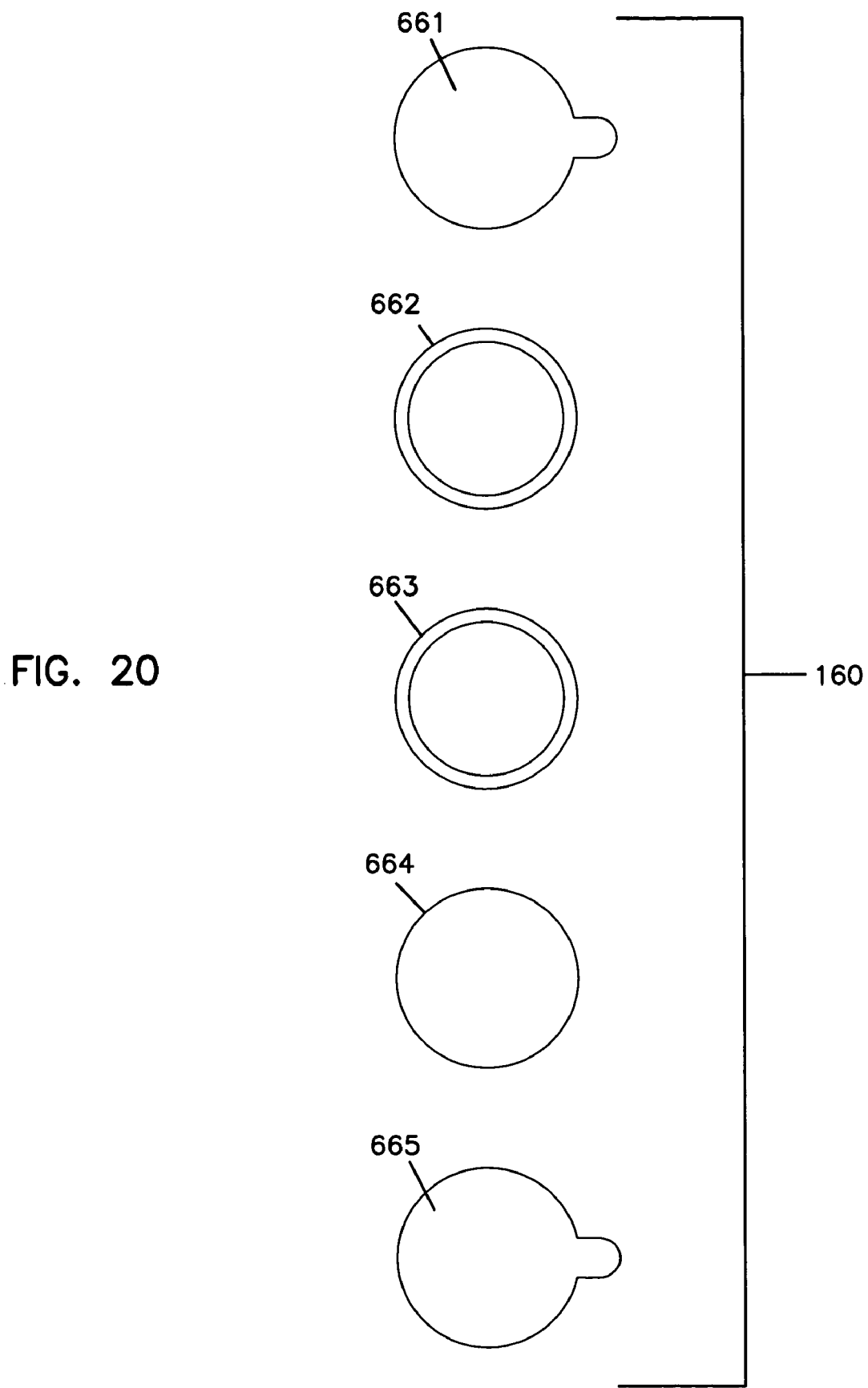
FIG. 20 is an exploded view of the adhesive portion of FIG. 18.

Referring now to FIGS. 18-20, an adhesive portion 160 is positioned on a surface 449 at the second end 442 of the sleeve 140 (see FIGS. 14 and 17). The surface 449 preferably acts as a framework that stabilizes the adhesive portion 160 prior to placement on the patient. In a preferred embodiment shown, the adhesive portion 160 includes layers 662, 663, and 664, as well as liners 661 and 665. Liners 661 and 665 also preferably include tabs 666 and 667 that allow for removal of the liners 661 and 665 as described below.

The adhesive portion 160 can be coupled to the surface 449 of sleeve 140 in a variety of manners. In a preferred embodiment, the liner 661 is removed, and layer 662 is coupled to the surface 449 using an adhesive. In addition, as described further below, in a preferred embodiment a top surface 669 of layer 664 and/or a lower end of the infusion device includes an adhesive to couple the infusion device to the adhesive portion 160 as the infusion device is moved into contact with the adhesive portion. See FIGS. 28A, 28B, and 28C.

In addition, the liner 665 is preferably removed, and a lower surface 668 of the layer 664 includes an adhesive to couple the adhesive portion 160 to the skin of the patient.

Preferably, the site is loaded into the device 100 prior to application of the adhesive portion 160 onto the device 100, and preferably both liners 661 and 665 are removed as described above prior to attachment of the adhesive portion to the sleeve 140 and coupling of the cap 170 to the housing 110. In this manner, the patient preferably does not need to remove any liners prior to application of the adhesive portion 160 to the skin and introduction of the site into the skin.

Preferably, the layer 664 does not include any holes, but instead is pierced by the needle 336 as the needle 336 is advanced towards the skin, as described further below. This configuration can enhance the fit between the adhesive portion 160 and the skin of the patient.

In a preferred embodiment, the adhesive portion 160 includes adhesive on one or more of surfaces 668 and 669 to allow the adhesive portion 160 to be coupled to the sleeve 140, site, and/or to the skin of the patient. Typical adhesives that can be used on the adhesive portion 160 include, without limitation, acrylic adhesive, synthetic rubber-based adhesive, acrylate adhesive, and silicone-based adhesive.

In example embodiments, the adhesive portion 160 includes films with adhesives thereon, such as a Tegaderm™ film manufactured by 3M™ or an IV3000™ film manufactured by Smith & Nephew. For example, in the preferred embodiment shown, the tape layer 662 is 3M™ 9731 tape, and layers 663 and 664 are 3M™ Tegaderm™ p/n 9842.

Figure 22:
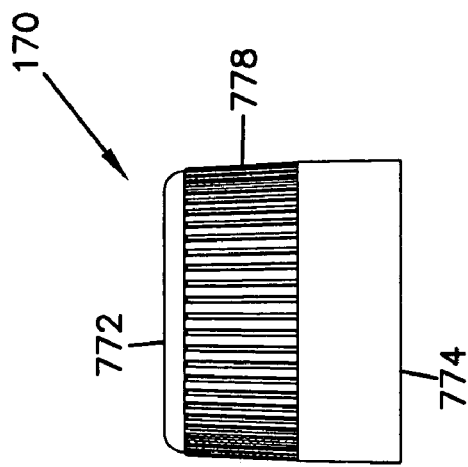
FIG. 22 is a side view of the cap of FIG. 21.
Figure 21:
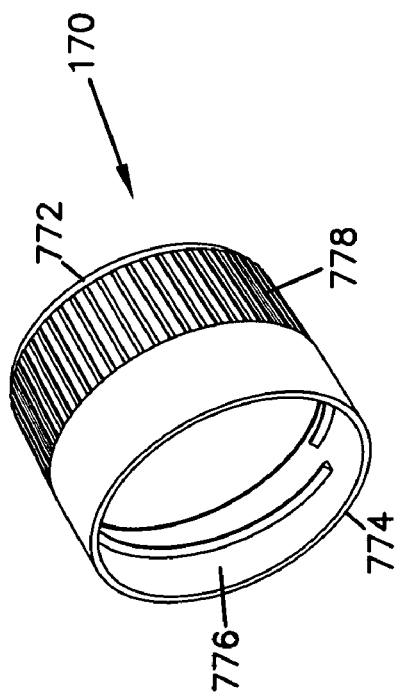
FIG. 21 is a perspective view of a cap of the device of FIG. 1.
Figure 23:
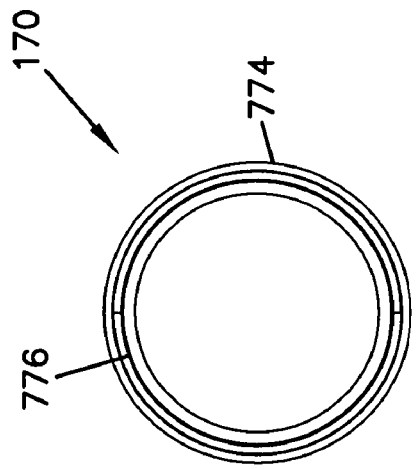
FIG. 23 is an end view of the cap of FIG. 21.

Referring now to FIGS. 21-23, the cap 170 is illustrated. The cap 170 includes a closed first end 772 and an open second end 774. The cap 170 preferably includes an exterior with a knurled surface 778 to enhance the patient's grip on the cap 170. In addition, the interior of the cap 170 includes a threaded portion 776 positioned adjacent the open second end 774 so that the threaded portion 776 can be threaded onto the threaded portion 113 of the housing 110 to seal the device 100. See FIGS. 1, 26A, and 26B.

In a preferred embodiment, a gasket 122 is provided on the threaded portion 113 of the housing 110 to create a seal between the cap 170 and the housing 110 as the cap 170 is threaded onto the housing 110. See FIGS. 26A and 26B. In this manner, the internal components of the device 100 (e.g., needle 336 and site 800) can be maintained in a substantially sterile state prior to removal of the cap 170. Further, the cap 170 can function to maintain the device 100 in a ship state (i.e., the housing 110 can not be moved relative to the sleeve 140) prior to removal of the cap 170 from the housing 110.

Figure 51:
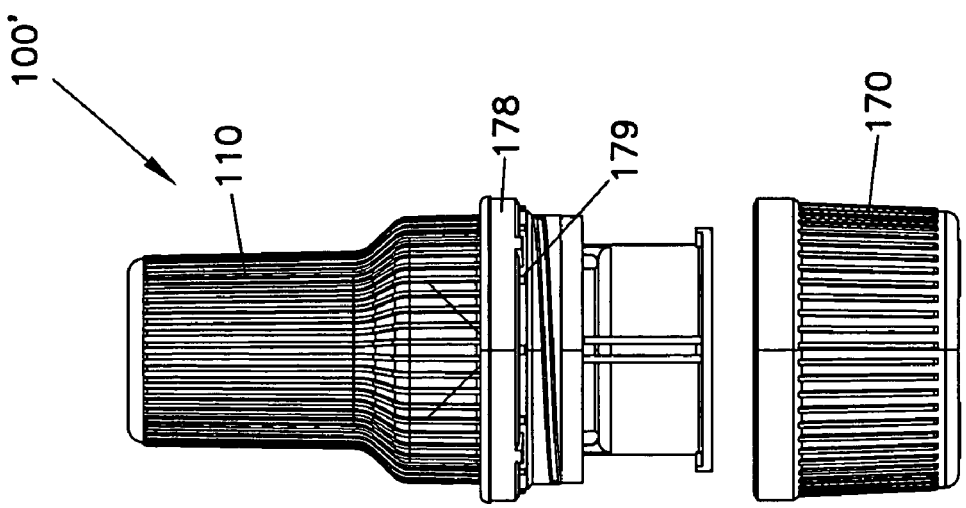
FIG. 51 is a side view of the device of FIG. 50 with the cap uncoupled and the tamper-evident seal having been broken.
Figure 50:
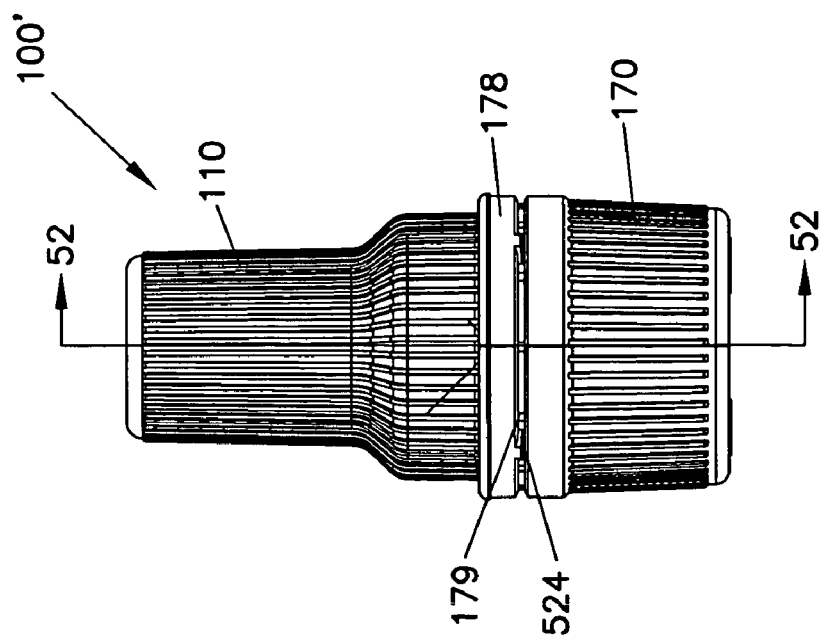
FIG. 50 is a side view of another example embodiment of a device used to introduce a cannula of an infusion device into a patient including a tamper-evident seal made in accordance with the present invention.

In alternative embodiments, the cap 170 and/or housing 110 can be formed to provide a tamper-evident seal so that the patient can determine when the cap 170 has been previously uncoupled from the housing 110. For example, in an alternative embodiment of the device 100' shown in FIGS. 50-52, a tamper-evident band 178 is shown. The band 178 includes tabs 179 that are coupled to the cap 170 as shown in FIG. 50. As the cap 170 is removed from the housing 110 (i.e., threads 514 on cap 170 are unthreaded from threads 512 on housing 110), the tabs 179 break away from the cap 170, and the seal 178 remains coupled to the housing 110, as shown in FIG. 51. If the cap 170 is later threaded back onto the device 100', the breaks between the tabs 179 and the cap 170 are evident, allowing the patient to identify that the cap 170 of the device 100' has been previously removed.

The cap 170 and band 178 can be placed on the device 100' during manufacturing as a single unit. For example, as shown in FIG. 52, the cap 170 and band 178 can be pushed onto the device 100' (note that threads 512 and 514 can be rounded to allow the cap 170 to be pressed onto the device 100') so that portion 520 of the band 178 passes over and engages shoulder 522 of the housing 110 to retain the band 178 on the housing 110 when the cap 170 is unthreaded and tabs 179 are broken. In addition, notches 524 formed periodically along the band 178 prevent the cap 170 from bottoming out against the band 178 as the cap 170 and band 178 are pushed onto the device 100' so that the tabs 179 remain intact. A portion 502 extending along an interior circumference of the cap 170 can also be formed to engage the outer surface of the housing 110 to create a seal between the housing 110 and the cap 170.

It can be desirable to provide a tamper-evident seal, for example, so that the patient can assure that the device 100' is has not been previously opened and is sterile prior to use. Other methods of indicating tampering can also be used.

As previously noted, the device 100 can be used to introduce a cannula of an infusion device into the subcutaneous layer of skin of the patient. In a preferred embodiment, the infusion device includes a site 800, the site 800 including a cannula for delivery of a substance into the subcutaneous layer of skin of the patient. Site 800 is linked by tubing (not shown) with a fluid source, such as an infusion pump (not shown) to deliver fluid to the patient through the cannula. In a preferred embodiment, the site 800 can be made in accordance with that disclosed in U.S. patent application Ser. No. 10/705,736 entitled "Subcutaneous Infusion Device and Method," filed on even date herewith, the entirety of which is hereby incorporated by reference. However, sites of other configurations can also be used.

Figure 24:
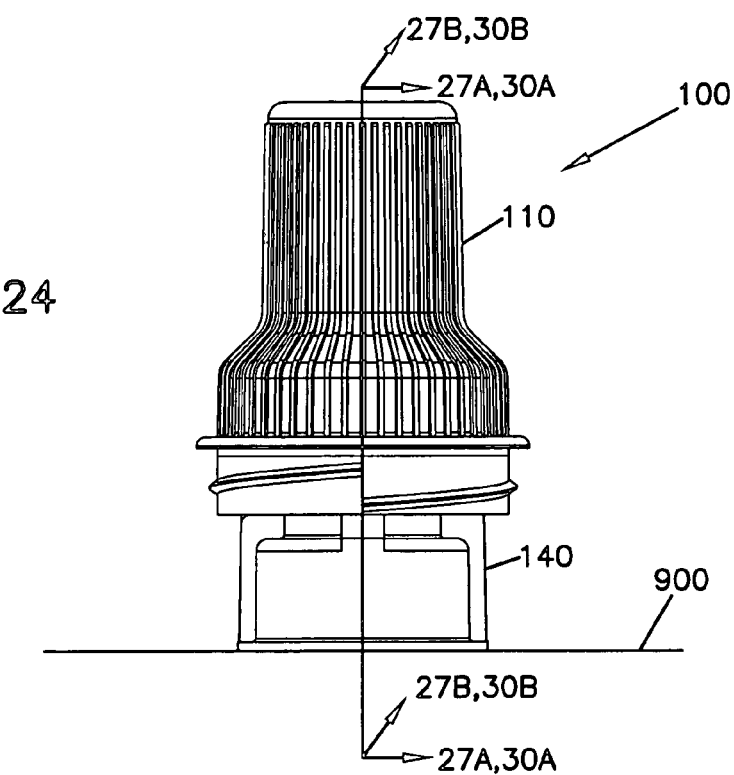
FIG. 24 is a side view of the device of FIG. 1 with the cap removed.
Figure 25:
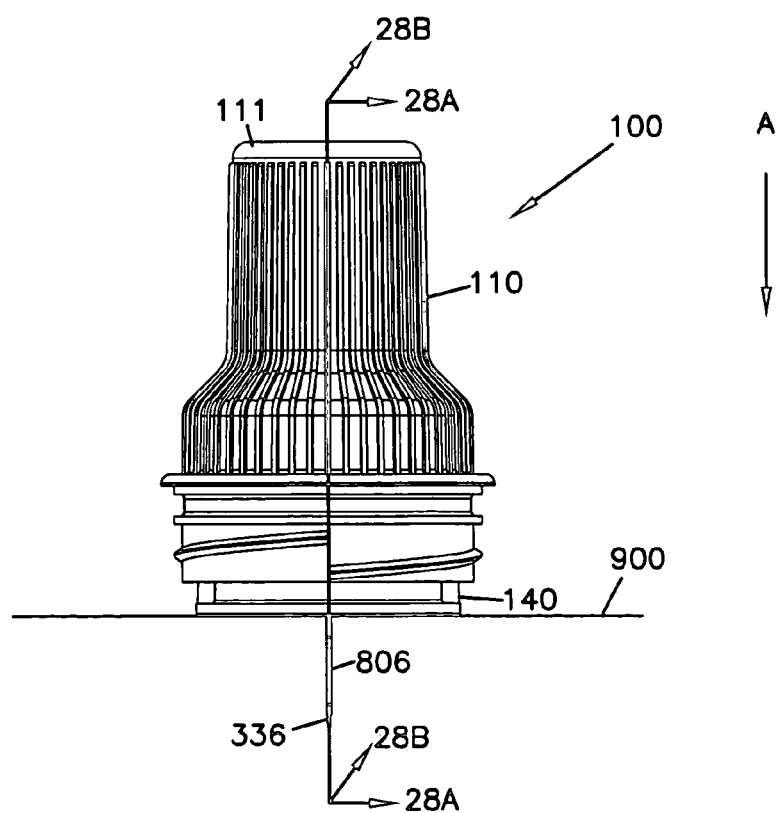
FIG. 25 is a side view of the device of FIG. 24 in a trigger state.

Referring now to FIGS. 1 and 24-30, the device 100 is illustrated in various states of use. As shown in FIGS. 1, 26A, and 26B, the device 100 is in a ship state prior to use. As shown in FIGS. 24, 27A, and 27B, the device 100 is in a delivery state ready to deliver the cannula of an infusion device into the skin of the patient. As shown in FIGS. 25, 28A, 28B, and 28C the device 100 is in a trigger state, or the state at which the needle 336 and the cannula of the site 800 have been fully inserted into the subcutaneous layer of skin of the patient, and the needle hub 130 and associated needle 336 are about to be retracted. As shown in FIGS. 29A and 29B, the device 100 is in a retracted state with the needle hub 130 and associated needle 336 having been retracted into the device 100. As shown in FIGS. 30A and 30B, the device 100 is in a fully retracted state with the housing 110 and sleeve 140 returned to an uncompressed position relative to one another.

An example method of use of the device 100 is as follows. The device 100 is provided to a patient with the cap 170 coupled to the housing 110, as shown in FIGS. 1, 26A, and 26B. Preferably, the site 800 has been previously loaded (i.e., preloaded) into the device 100 during, for example, the manufacturing process for the device 100.

The cap 170 is then unthreaded from the housing 110, and the sleeve 140 of the device 100 is positioned so that the adhesive portion 160 (i.e., surface 668) contacts the skin 900 of the patient. See FIGS. 24, 27A, and 27B.

Next, in the illustrated preferred embodiment, the patient applies pressure to the upper end 111 of the housing 110 to move the housing 110 and associated structures including the cylinder hub 120 and needle hub 130 (including needle 336 and site 800) in a direction A with respect to the sleeve 140 and toward the skin 900 of the patient. As the needle 336 of the needle hub 130 and associated site 800 are moved in the direction A, the needle 336 and the cannula 806 of the site 800 are introduced into the skin 900 of the patient. In addition, as the needle hub 130 is moved toward the sleeve 140, the spring 150 is further compressed.

Once the needle 336 and cannula 806 of the site 800 have been fully inserted into the skin 900, the device 100 is in a trigger state, as illustrated in FIGS. 25, 28A, 28B, and 28C. In this state, the barbs 335 that couple the needle hub 130 to the cylinder hub 120 are biased inwardly through contact with the projections 444 formed by the sleeve 140.

Figure 28C:
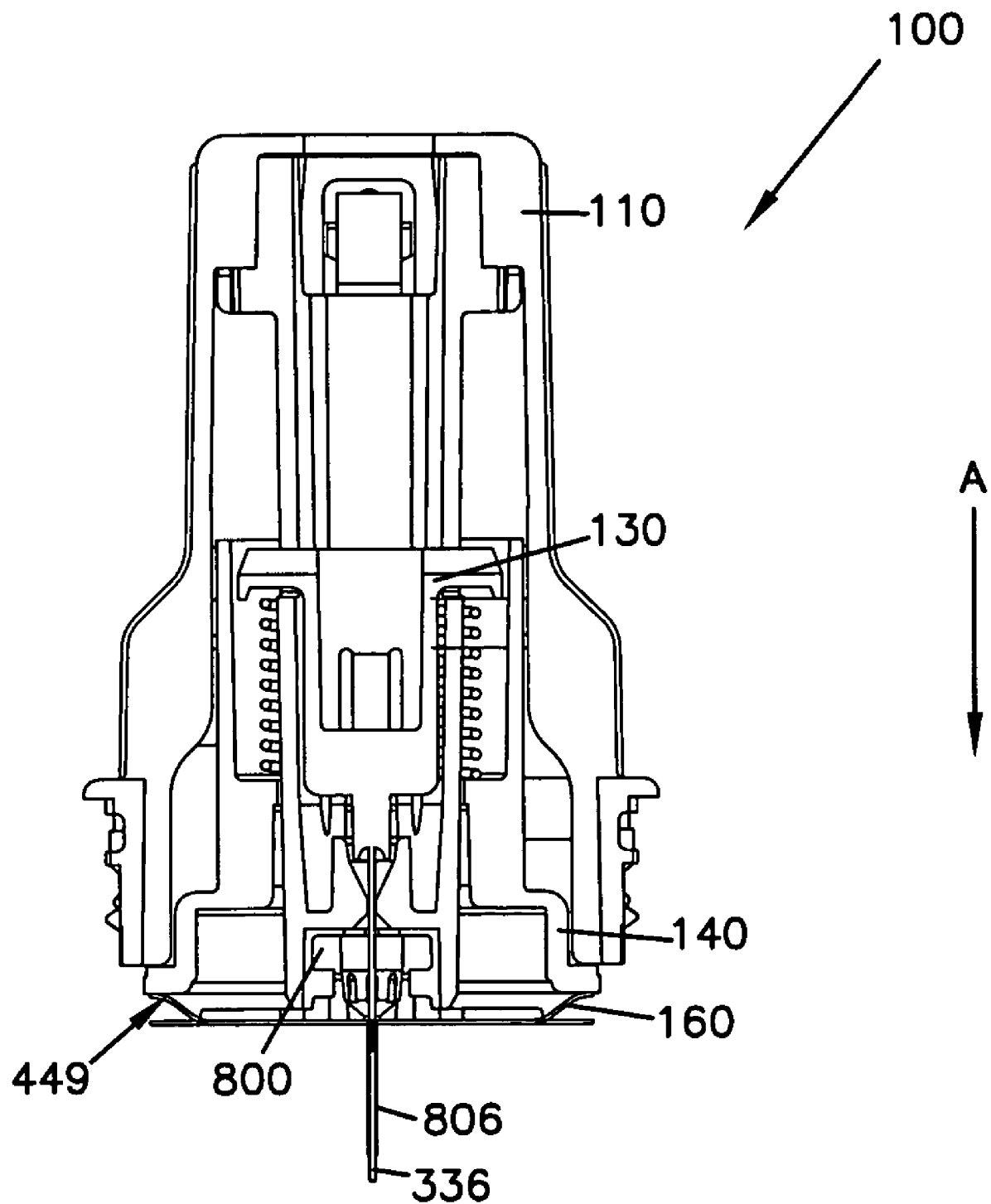
FIG. 28C is a cross-sectional view of the device of FIG. 28B illustrating the adhesive portion being sheared from a surface of the sleeve.

As the housing 110, cylinder hub 120, and needle hub 130 are displaced further in the direction A, it is preferable that the needle hub 130 is positioned so that a lower portion of the site 800 travels slightly beyond the second end 442 of the sleeve 140 as shown in FIG. 28C. This "over-travel" assures that the adhesive portion 160 is properly sheared away from the surface 449 of the sleeve 140 and allows for the coupling of the site 800 to the adhesive portion 160. For example, in preferred embodiments, the lower portion of the site 800 travels beyond the second end 442 of the sleeve 140 by between 50 to 100 thousandths of an inch, more preferably approximately 70 thousandths of an inch.

In addition, as the housing 110, cylinder hub 120, and needle hub 130 are displaced further in the direction A as described above, barbs 335 of the needle hub 130 are forced inwardly by the projections 444 of the sleeve 140, and the barbs 335 are thereby uncoupled from engagement with the cylinder hub 120. Once the barbs 335 of the needle hub 130 are released from the cylinder hub 120, the needle hub 130 is free to move longitudinally within the passage 223 of the cylinder hub 120 in a direction B opposite to that of the direction A. The spring 150, which has been compressed through the movement of the housing 110 in the direction A, propels the needle hub 130 and associated needle 336 in the direction B up through the cylinder hub 120 into the upper end 111 of the housing 110, while leaving the site 800 and associated cannula 806 positioned in the skin 900 of the patient, as shown in FIGS. 29A and 29B.

Once the patient removes pressure from the upper end 111 of the housing 110, the spring 150 causes the housing 110 and cylinder hub 120 to move in the direction B as shown in FIGS. 30A and 30B to a fully retracted state.

Finally, the sleeve 140 is removed from contact with the skin 900, and the cap 170 can be replaced onto the threaded portion 113 of the housing 110 of the device 100. Subsequently, the device 100 can be discarded.

Figure 31:
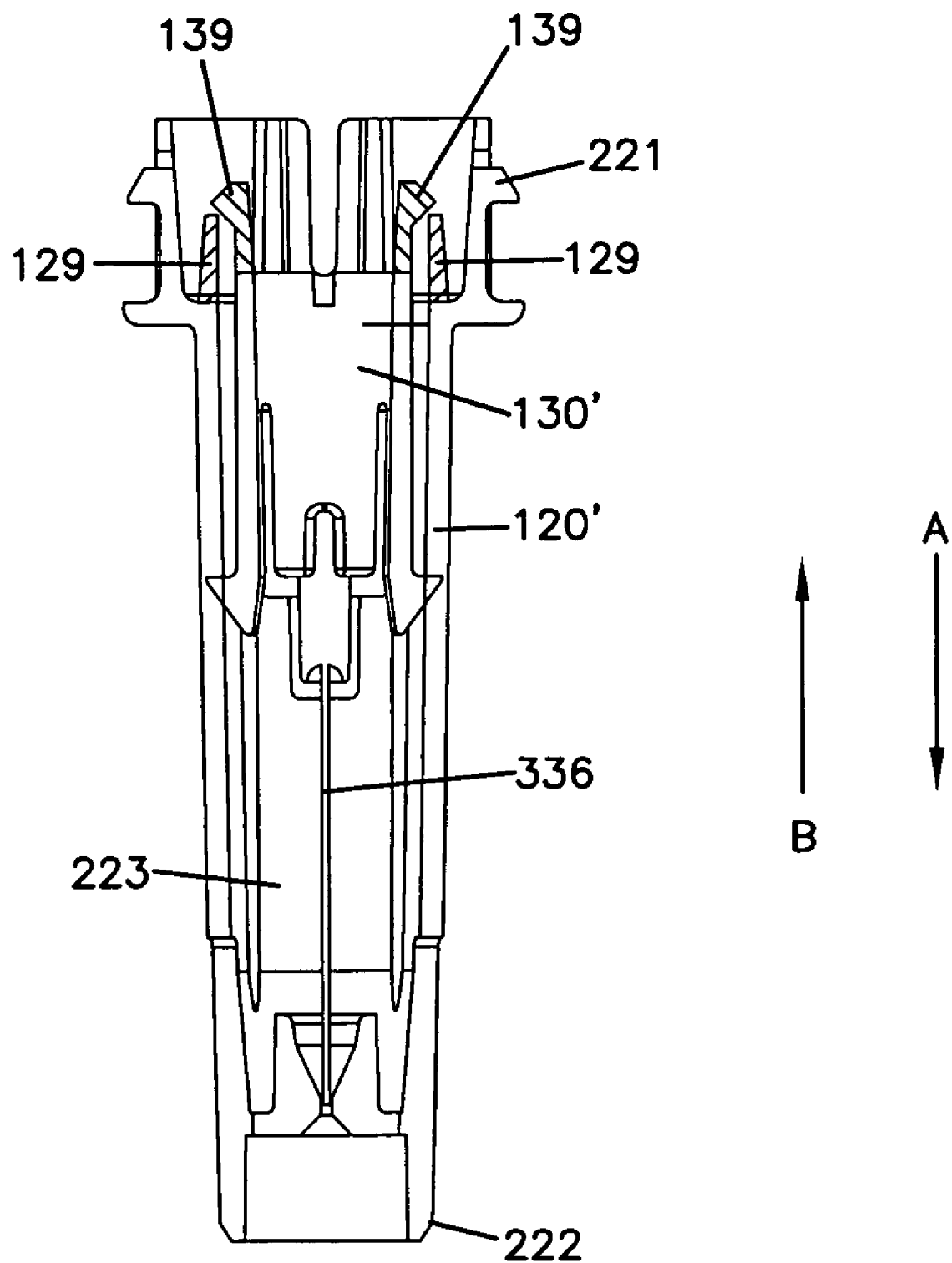
FIG. 31 is a cross-sectional view of a portion of another example embodiment of a device used to introduce an infusion device into a patient made in accordance with the present invention.
Figure 32A:
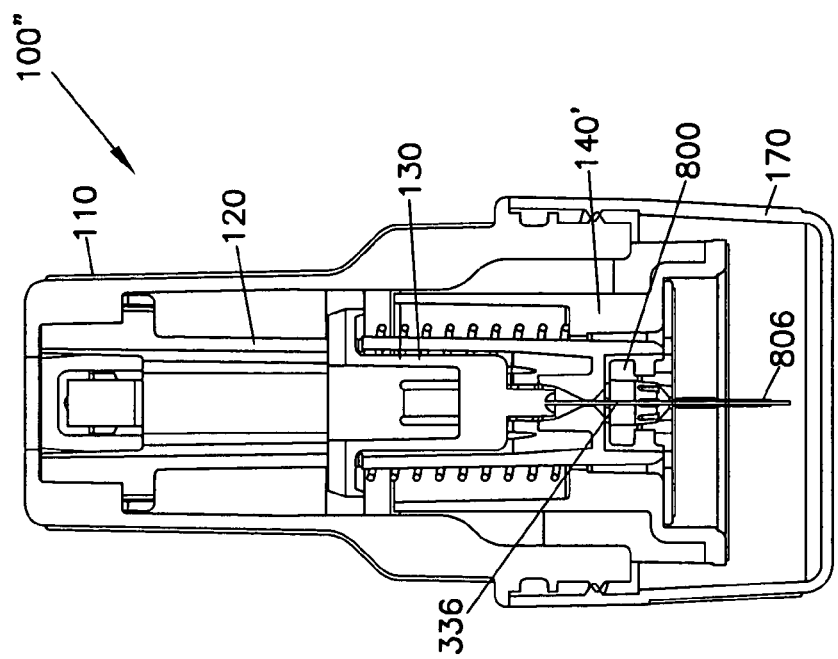
FIG. 32A is a cross-sectional view of another example embodiment of a device used to introduce an infusion device into a patient in a ship state made in accordance with the present invention.
Figure 32B:
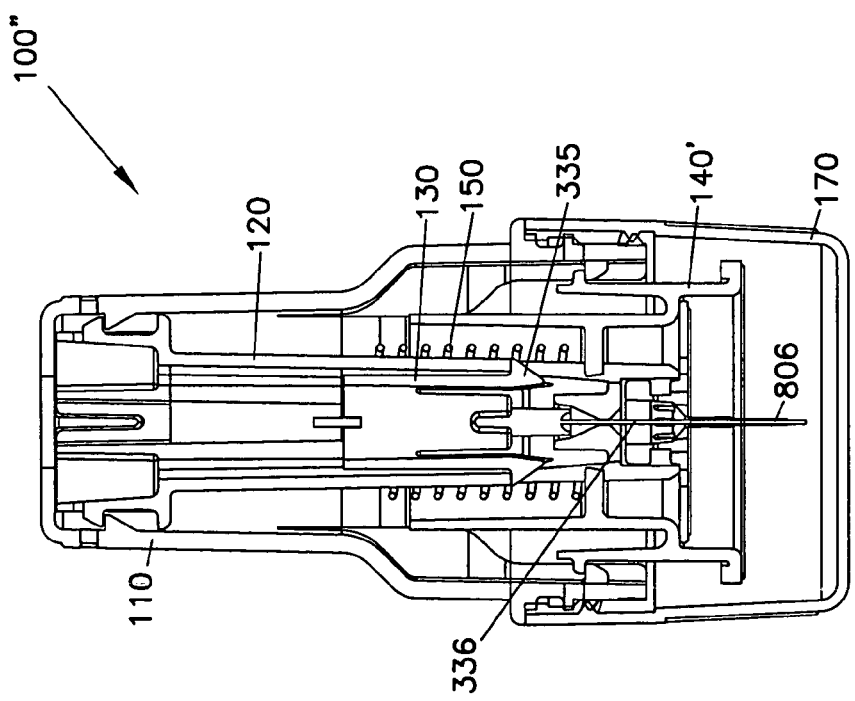
FIG. 32B is a cross-sectional view along a perpendicular plane of the device of FIG. 32A.
Figure 37:
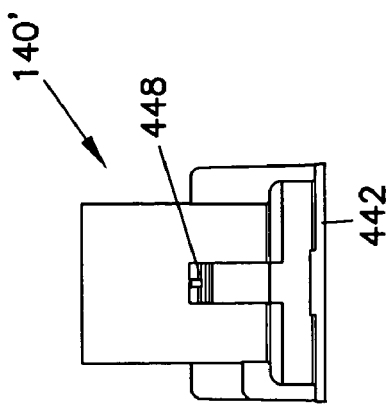
FIG. 37 is another side view of the sleeve of FIG. 35.
Figure 36:
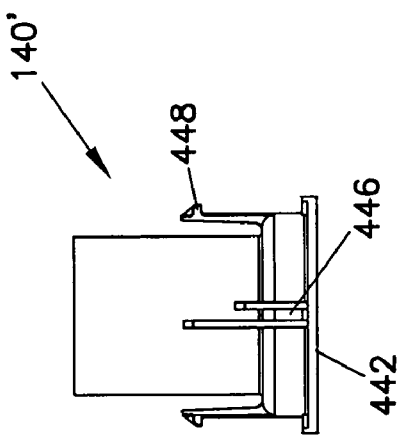
FIG. 36 is a side view of the sleeve of FIG. 35.
Figure 38:
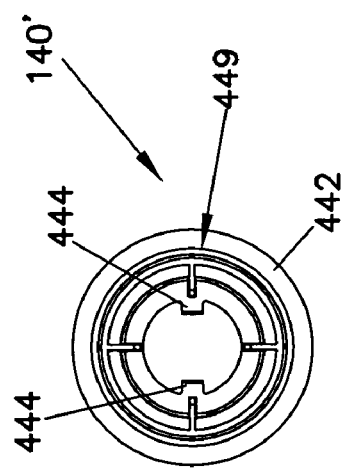
FIG. 38 is an end view of the sleeve of FIG. 35.
Figure 35:
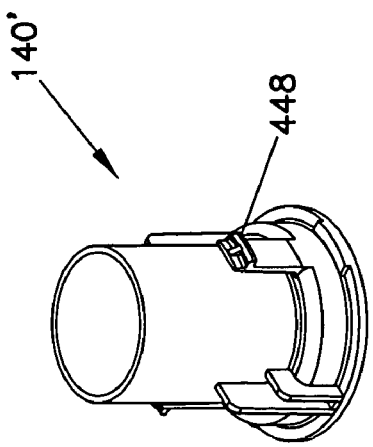
FIG. 35 is a perspective view of a sleeve of the device of FIG. 32A.
Figure 40:
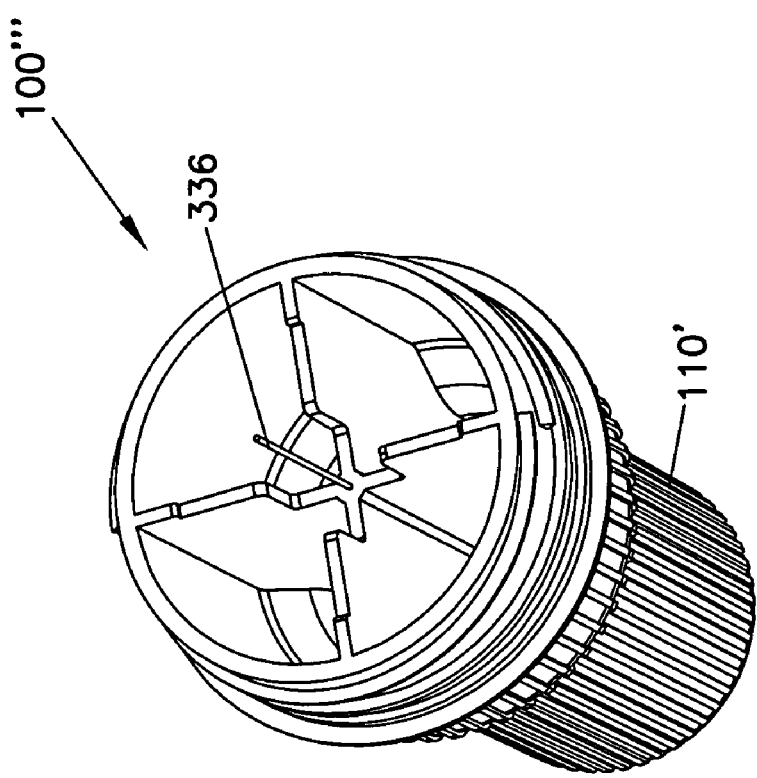
FIG. 40 is another perspective view of the device of FIG. 39.
Figure 39:
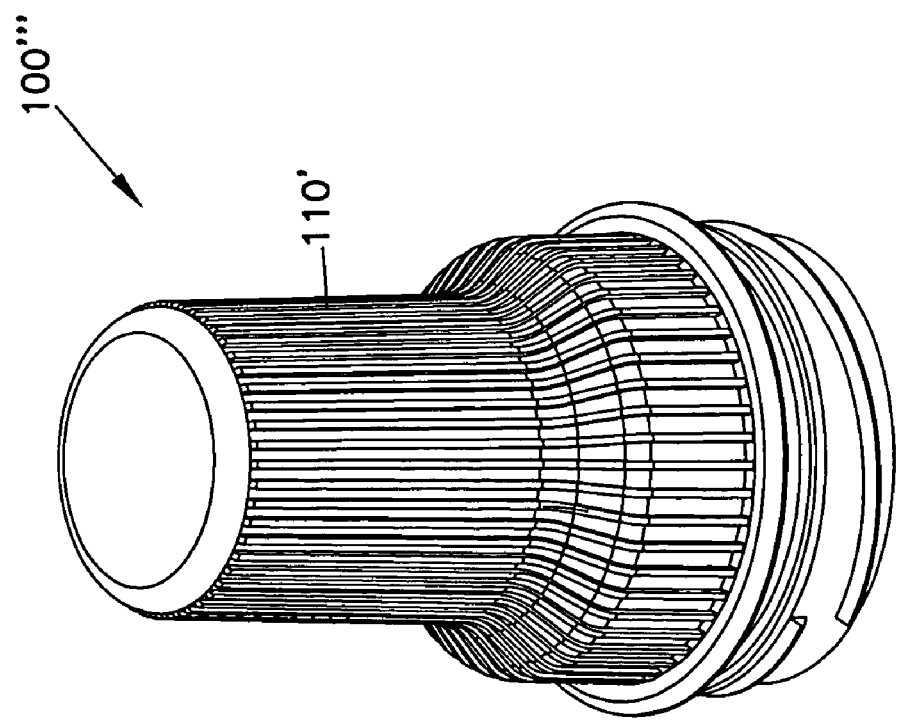
FIG. 39 is a perspective view of another example embodiment of a device used to introduce an infusion device into a patient made in accordance with the present invention.
Figure 44:
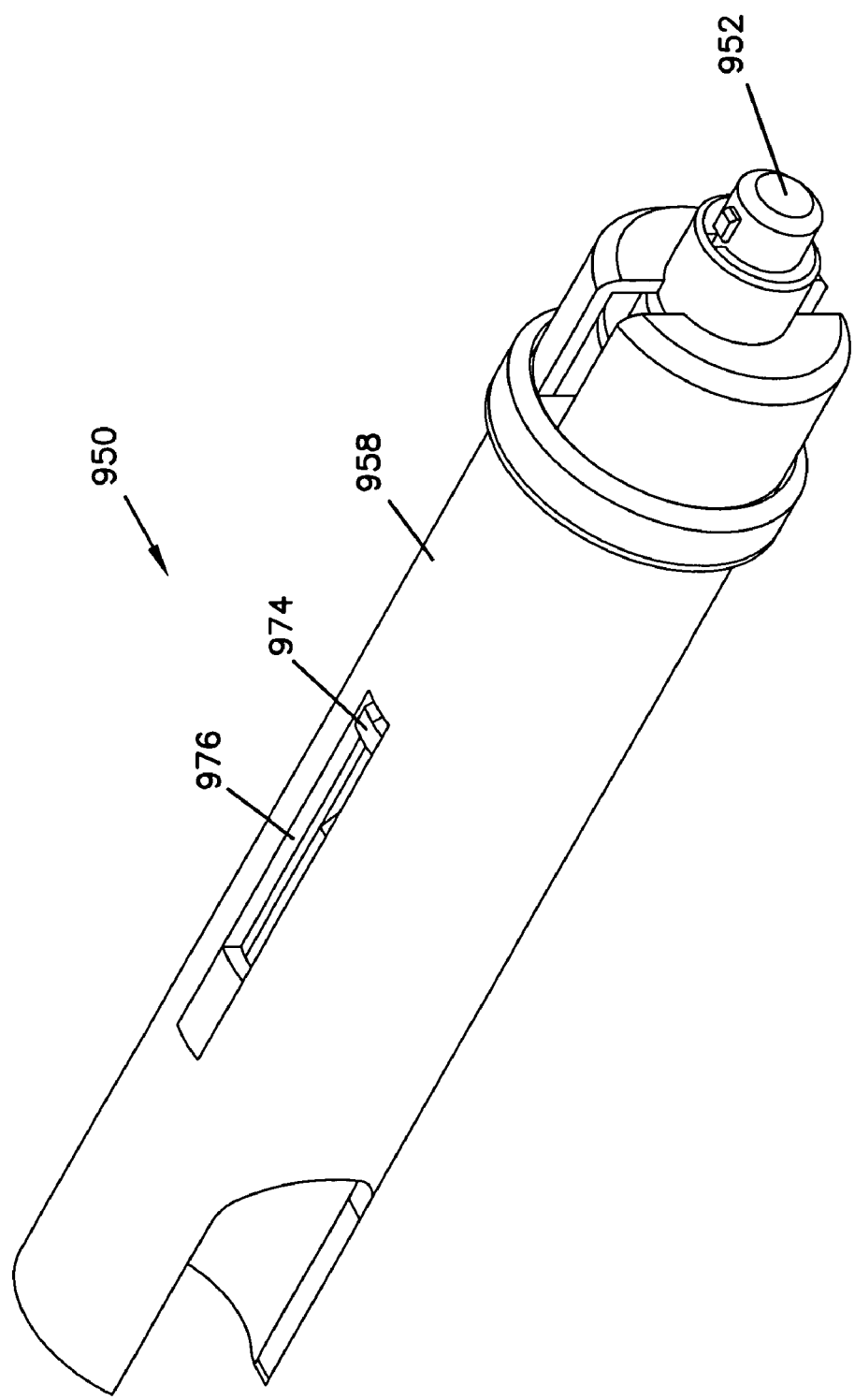
FIG. 44 is a perspective view of another example embodiment of a device used to introduce an infusion device into a patient made in accordance with the present invention.
Figure 45:
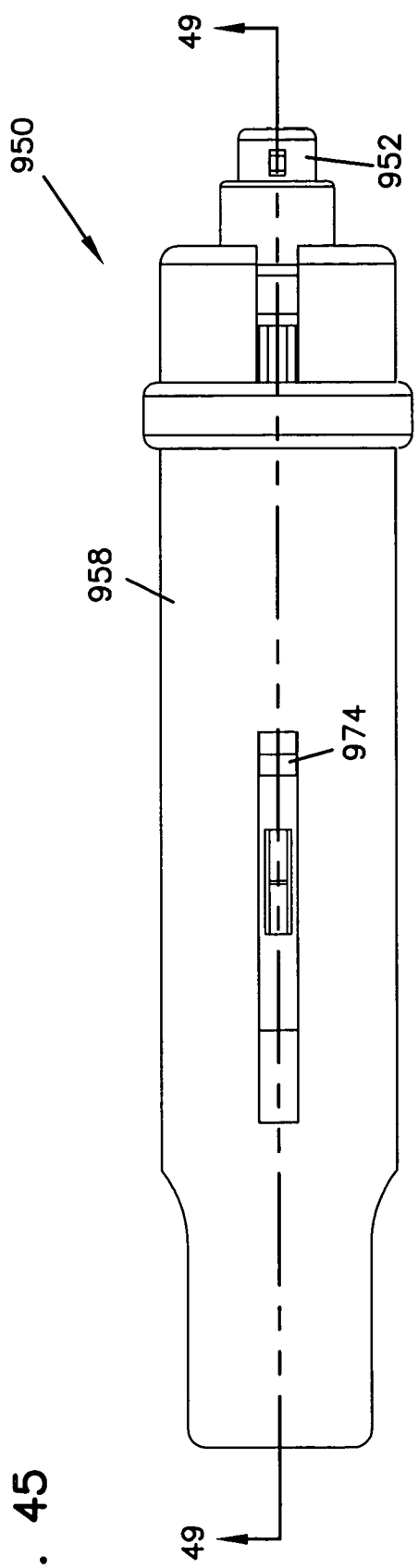
FIG. 45 is a side view of the device of FIG. 44.
Figure 46:
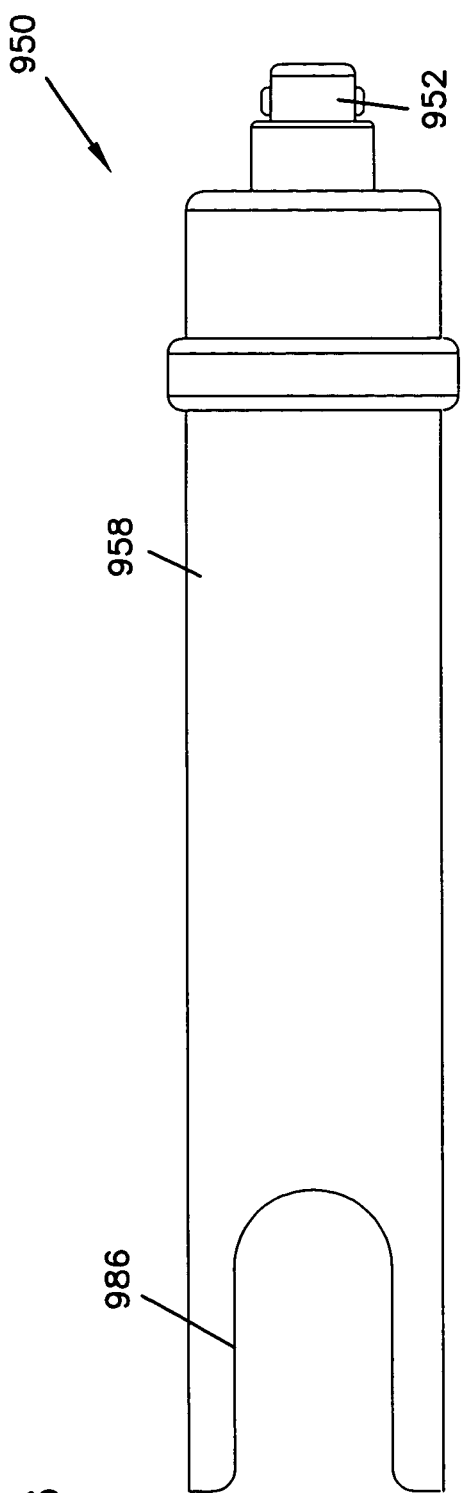
FIG. 46 is another side view of the device of FIG. 44.
Figure 48:
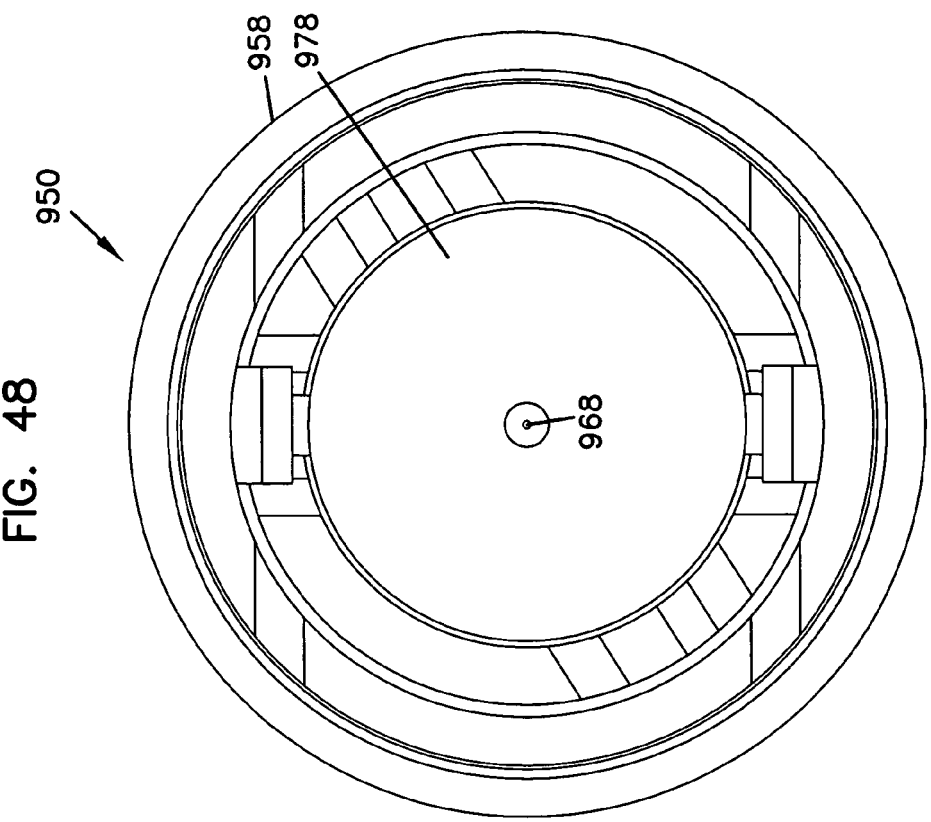
FIG. 48 is another end view of the device of FIG. 44.
Figure 47:
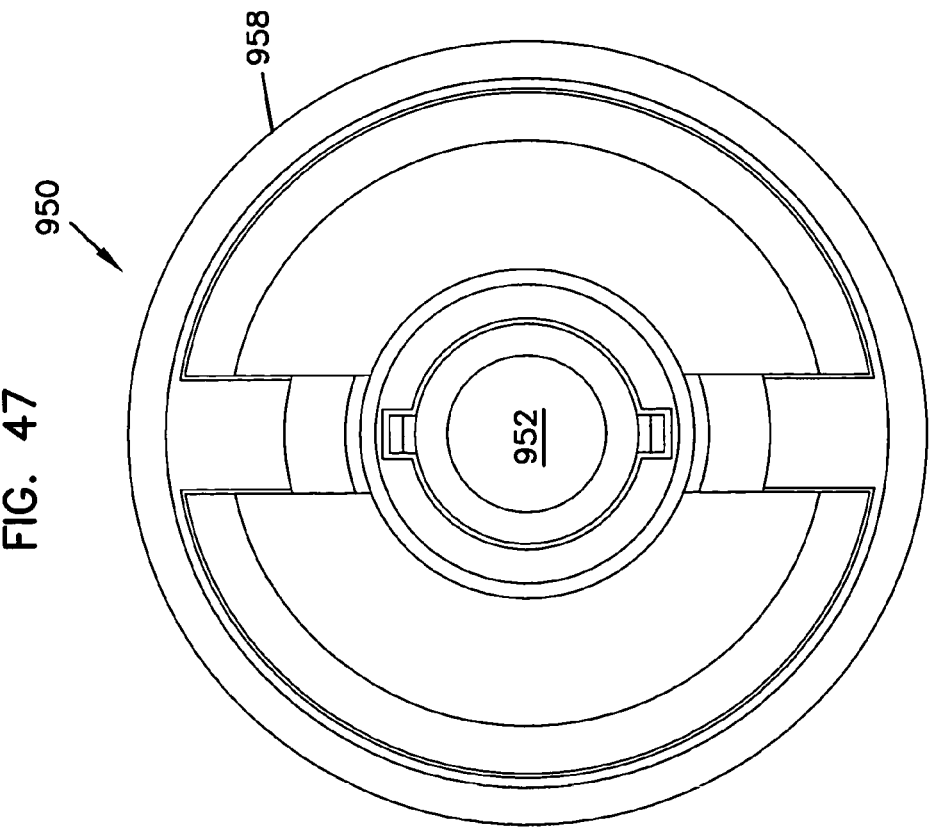
FIG. 47 is an end view of the device of FIG. 44.

Many alternative designs for the device can be provided. For example, in FIG. 31 a portion of an alternative device is shown including cylinder hub 120' and needle hub 130'. The cylinder hub 120' and needle hub 130' are similar to cylinder hub 120 and needle hub 130 described above, except that the cylinder hub 120' includes projections 129 formed near the first end 221 of the cylinder hub 120', and the needle hub 130' includes barbs 139 formed on the first end 332. The barbs 139 are configured to ride inside the interior passage 223 of the cylinder hub 120' during retraction of the needle 336 in the direction B until the barbs 139 extend beyond the projections 129 of the cylinder hub 120'. Once this occurs, the barbs 139 expand outward slightly. In this configuration as shown in FIG. 31, the barbs 139 prevent the needle hub 130' and associated needle 336 from being moved back in the direction A. In this manner, the barbs 129 lock the needle hub 130' in the retracted position. This configuration can be beneficial, used separately or in conjunction with the force of the spring 150 forcing the needle hub 130' in the direction B, to further reduce the possibility of inadvertent exposure to the needle 336 after retraction.

According to another alternative embodiment, a device 100" is illustrated in FIGS. 32-38. Device 100" is similar to device 100 described above, except that the sleeve (e.g., sleeve 140) is replaced with a trigger 140'. In device 100", the trigger 140' (see FIGS. 35-38) does not function as sleeve 140 to shroud the needle 336 prior to insertion, but instead trigger 140' functions to cause retraction of the needle 336 upon full insertion, as described further below.

In this embodiment of device 100", once the cap 170 has been removed, needle 336 is exposed as shown in FIGS. 33A and 33B. In this configuration, instead of moving the housing 110, cylinder hub 120, and needle hub 130 longitudinally with respect to the housing, the patient simply inserts the needle 336 and associated cannula 806 of the site into the skin by grasping the housing 110 and introducing the exposed needle 336 into the skin.

As the needle 336 and cannula 806 reaches full insertion, the trigger 140' contacts the skin and thereby causes the needle hub 130 including the needle 336 to be retracted into the housing 110, leaving the site 800 in place on the skin. In the illustrated embodiment, the trigger 140' is automatic, in that the trigger 140' is configured to cause barbs 335 of the needle hub 130 to be displace inwardly to release the needle hub 130 from the cylinder hub 120, and the spring 150 can thereupon move the needle hub 130 and associated needle 336 in the direction B into an upper portion of the housing 110 as shown in FIGS. 34A and 34B.

In alternative embodiments, the trigger 140' can be configured to be manually actuated by the patient to cause retraction of the needle hub 130 and associated needle 336 once the cannula 806 has been fully inserted.

Referring now to FIGS. 39-43, another embodiment of a device 100''' is shown. The device 100''' is a manual device in that the device 100''' includes only a housing 110', needle 336, and cap (not shown) that can be threaded onto the housing 110'. Preferably, a site (not shown) can be preloaded onto the needle 336 and the cap placed on the housing 110' to create a sterile environment prior to use. To use device 100''', the patient preferably removes the cap from the housing 110' and, holding the housing 110' inserts the needle and associated cannula of the site into the skin. Once the cannula is completely inserted, the patient moves the housing 110' in the opposite direction to remove the needle from the skin while leaving the site in place. Finally, the patient preferably reapplies the cap to the housing 110' to reduce the chance for further inadvertent exposure to the needle 336. The device 100''' can then be discarded or reused as desired.

Referring now to FIGS. 44-49, another example embodiment of a device 950 for assisting in the introduction of a site 970 is shown. The device 950 differs from the device 100. For example, while the device 100 can be manually driven by the patient to insert the needle and cannula of the site into the skin, the device 950 is automated in that a spring 960 is used to drive the needle and cannula of the site into the skin of the patient.

The device 950 includes a housing 958, cap 952, lock member 962, needle hub 965, main body 980, retainer body 978, and sleeve 982. Also included are the first spring 960 and a second spring 966.

The device 950 functions as follows. The lock member 962, needle hub 964, and retainer body 978 are moveable longitudinally with respect to the housing 958 and sleeve 982 of the device 950. The lock member 962 is positioned so that needle 968 of the needle hub 965 is accessible from open end 984 of the device 950. The site 970 can then be loaded onto the needle 968 by threading the cannula of the site 970 onto the needle 968. Openings 986 are formed by the housing 958 to accommodate sites 970 of various sizes (e.g., wings formed on sites).

Figure 49:
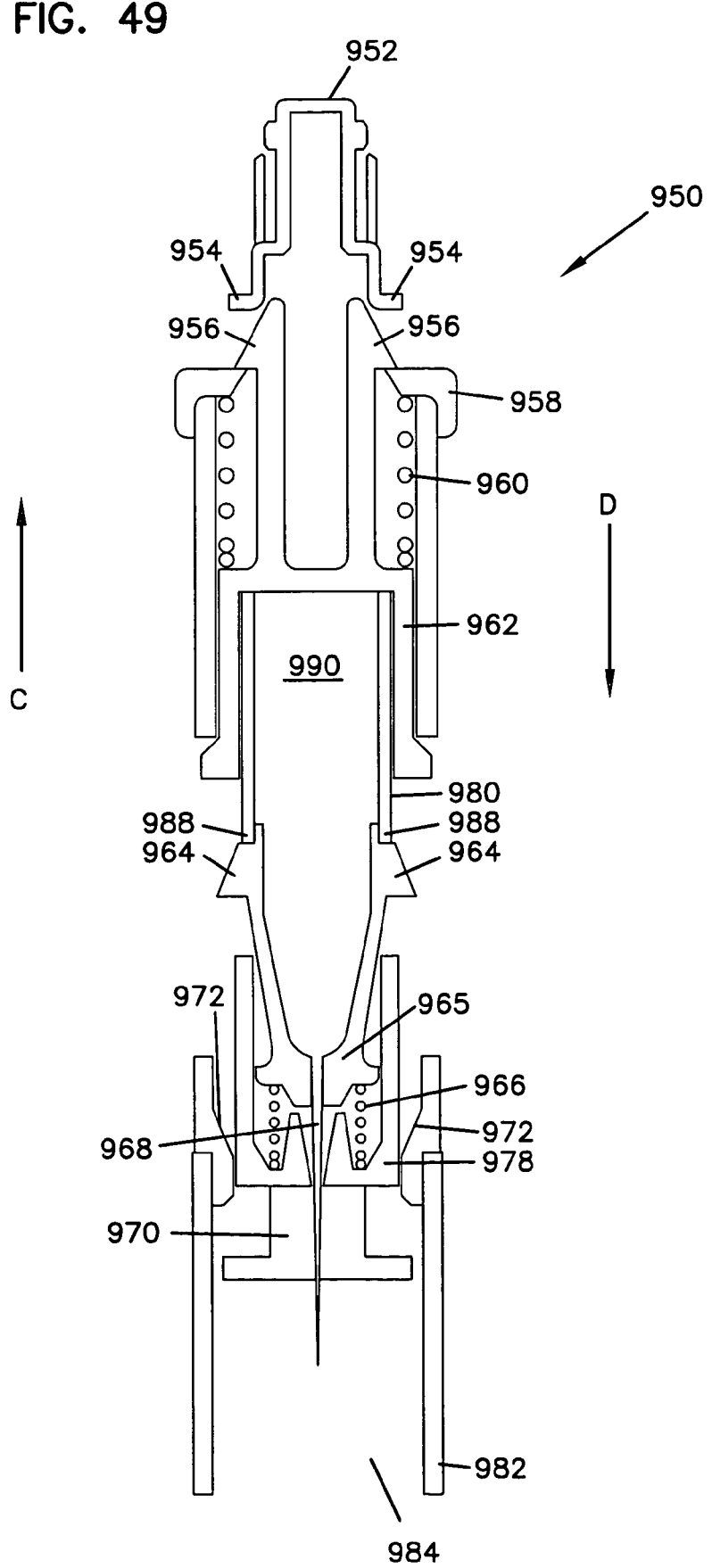
FIG. 49 is a cross-sectional view taken along line 49-49 of the device of FIG. 45.

Once the site 970 has been loaded onto the needle 968, the lock member 962 is moved in a direction C by the patient using projections 974 that are accessible through slot 976 of housing 958 until barbs 956 of the lock member 962 engage an outer surface of the housing 958, as shown in FIG. 49. In this position, the device 950 is ready to insert the site 970 into the skin of the patient.

Next, the sleeve 982 of the device 950 is placed against the skin of the patient. To initiate insertion of the site 970, the cap 952 is pressed by the patient. Once pressed, shoulders 954 on an opposite end of the cap 952 engage and push the barbs 956 of the lock member 962 toward one another to disengage the barbs 956 from the housing 958. When the barbs 956 clear the housing 958, the lock member 962, main body 980, needle hub 965, retainer body 978, and associated site 970 are moved by the first spring 960 a the direction D.

The device 950 continues to move the site 970 towards the skin, thereby introducing the needle 968 and cannula of the site 970 into the skin. As the cannula of the site 970 is fully inserted into the skin, barbs 964 of the needle hub 965 engage ramped surfaces 972 of the sleeve 982, causing the barbs 964 to be forced toward one another. When the cannula of the site 970 is fully inserted into the skin, the barbs 964 have been forced inwardly by the surfaces 972 sufficiently to clear ends 988 of the main body 980, and the second spring 966 moves the needle hub 965 in the direction C into a passage 990 formed by the main body 980.

As the needle hub 965 is moved by the second spring 966 into the main body 980, the needle 968 is removed from the site 970, leaving the site 970 in place on the skin. In addition, the retainer body 978 remains in a position adjacent the open end 984 of the sleeve 982 so that once the device 950 is removed from the skin of the patient, the retainer body 978 protects the patient from further contact with the needle 968.

Devices made in accordance with the principles described herein can be advantageous for various reasons. For example, each device can provide ease in placement of the site on the skin, preferably allowing the user to place the site with the device where desired on the body using a single hand to operate the device.

Further, several embodiments disclosed herein include structures that cover or hide the needle prior to insertion of the site, and also cause the needle to be retracted into the device after insertion to protect against inadvertent contact with the needle.

In addition, several embodiments of the devices disclosed herein can automatically retract the needle while leaving the site placed on the skin, thereby reducing the patient's contact with the exposed needle. Preferably, this retraction is automatic in that once the device reaches the trigger state there is no further action required by the patient to cause the needle to be retracted. The automatic retraction of the needle also limits the dwell time of the needle in the patient, increasing comfort for the patient.

In addition, the action of inserting the needle into position on the skin using the devices disclosed herein can function to hold the site on the surface of the skin during needle retraction. This can assist in adherence of the adhesive portion to the skin and reduce the chances of separation between the adhesive portion and site and the skin during needle retraction.

In addition, the housing and cap of several of embodiments of the devices disclosed herein allow the various components of the devices including the needle and infusion device to be delivered to the patient in a self-contained, sterile environment prior to use. The configuration further minimizes the need for packaging surrounding the devices, reducing manufacturing cost and increasing ease in use of the devices. The configuration also allows the housing and cap to protect and maintain the infusion device on the needle of the device. The configuration and disposable nature of the devices further allow ease in discarding of the devices after use.

Also, the configuration of several embodiments of the devices disclosed herein can allow the site to be preloaded into the device, thereby providing ease of use for the patient and reducing the patient's exposure to the needle. For example, single-use embodiments disclosed herein preferably do not require that the patient load the site into the device prior to insertion, but instead provide the device with the site preloaded.

Some embodiments of the devices allow for both automatic delivery of the site and withdrawal of the needle, thereby automating the entire introduction process for the patient.

While single use devices are preferred, reusable devices wherein the needle retracts but can be reloaded are also anticipated.

The above specification, examples and data provide a complete description of the manufacture and of the invention. Since many embodiments of the invention can be made without departing from the spirit and scope of the invention, the invention resides in the claims hereinafter appended.

What is claimed is:

1. A device for automatically retracting a needle used to introduce a cannula of a subcutaneous infusion device into a subcutaneous layer of skin of a patient, the device comprising:
   a housing defining an internal cavity;
   a needle hub coupled to the housing and including a needle, the needle being coupled to a cannula of a subcutaneous infusion device, and the needle hub including barbs coupling the needle hub to the housing;
   a spring configured to move the needle into a retracted state; and
   a trigger member including projections;
   wherein, upon full introduction of the needle and associated cannula of the subcutaneous infusion device into a subcutaneous layer of skin of a patient, the projections come in contact with the barbs of the needle hub and force the barbs to release the needle hub from the housing, and the spring automatically moves the needle hub and associated needle into the internal cavity of the housing into the retracted state while leaving the cannula of the subcutaneous infusion device in the subcutaneous layer of skin of the patient.

2. The device of claim 1, further comprising a second spring configured to introduce the needle and associated cannula of the subcutaneous infusion device into the subcutaneous layer of skin of the patient.

3. The device of claim 1, wherein the housing includes a first portion coupled to the needle, and a second portion that is slideably received in the first portion, wherein the first portion slides relative to the second portion to introduce the needle into the subcutaneous layer of skin of the patient.

4. The device of claim 1, further comprising means for covering the needle prior to introduction of the needle into the subcutaneous layer of skin of the patient.

5. The device of claim 1, further comprising a sleeve coupled to the housing to cover the needle prior to introduction of the needle into the subcutaneous layer of skin of the patient.

6. The device of claim 1, wherein the device is configured to allow the subcutaneous infusion device to be preloaded into the device.

7. The device of claim 1, further comprising a cap that is coupled to the housing of the device.

8. The device of claim 7, wherein the cap includes a tamper-evident seal.

9. A device for inserting a subcutaneous infusion device into skin of a patient, comprising:
   a housing;
   a hub coupled to the housing and defining an interior passage;
   a needle hub including a needle, the needle hub being positioned in the interior passage of the hub and including barbs that couple the needle hub to the housing so that the needle hub is held in a fixed position relative to the hub and the housing;
   a sleeve;
   a spring engaging the needle hub;
   a trigger member including projections; and
   a cap configured to be coupled to the housing, the cap including a tamper-evident band,
   wherein the tamper-evident band remains coupled to the housing when the cap is removed from the housing;
   wherein the housing, hub, and needle hub are movable relative to the sleeve to introduce the needle of the needle hub and associated cannula of an infusion device into a subcutaneous layer of skin, and wherein, upon the needle and associated infusion device being fully inserted into the subcutaneous layer of skin, the projections come in contact with the barbs of the needle hub and force the barbs to release the needle hub so that the needle hub is slideable relative to the hub, and the needle hub including the needle are moveable by the spring through the passage of the hub to a retracted state, leaving the infusion device positioned on the skin of the patient.

10. The device of claim 9, further comprising another spring engaging the needle hub, the spring being positioned to automatically introduce the needle of the needle hub and associated cannula of the infusion device into the subcutaneous layer of the skin of the patient.

11. The device of claim 9, wherein the device is configured to allow the subcutaneous infusion device to be preloaded into the device.

12. A device for inserting a subcutaneous infusion device into skin of a patient, comprising:
   a housing including a closed upper end, defining an open lower end, and a threaded portion positioned adjacent the open lower end;
   a cylinder hub including first and second ends, the cylinder hub defining an interior passage and two opposing slots extending from a mid-portion of the hub to the first end, and the cylinder hub defining opposing apertures adjacent the second end of the cylinder hub, wherein the first end of the cylinder hub is coupled to the upper end of the housing;
   a needle hub including a main body with first and second ends, and a needle coupled to the main body, the main body including opposing wings formed at the first end and opposing barbs at the second end, wherein the needle hub is positioned in the interior passage of the cylinder hub such that the opposing wings extend through the opposing slots of the cylinder hub, and the opposing barbs of the needle hub extend through the opposing apertures of the cylinder hub and engage the cylinder hub so that the needle hub is held in a fixed position relative to the cylinder hub and the housing;
   a sleeve including first and second ends and defining an interior passage, the sleeve including opposing projections extending inwardly into the interior passage of the sleeve at a mid-portion of the sleeve, and a cylindrical shoulder formed in the interior passage at the mid-portion of the sleeve, wherein the second end of the cylinder hub extends through the passage of the sleeve, and a portion of the sleeve including the first end is received within the housing;
   a spring with first and second ends, wherein the spring surrounds the cylinder hub and extends within the passage of the sleeve, and wherein the first end of the spring is seated on the shoulder of the sleeve, and the second end of the spring engages the opposing wings of the needle hub extending through the opposing slots of the cylinder hub; and
   a cap including a closed first end, defining an open second end, and a threaded portion positioned adjacent the open second end, wherein the threaded portion of the cap is threaded onto the threaded portion of the housing to seal the device;
   wherein, upon removal of the cap from the housing, the second end of the sleeve is positioned relative to skin of a patient, and the housing, cylinder hub, and needle hub are moved relative to the sleeve in a direction towards the skin of the patient so that the needle of the needle hub and associated cannula of an infusion device are introduced into a subcutaneous layer of the skin, and wherein, upon the needle and associated infusion device being fully inserted into the skin and the cylinder hub being moved relative to the sleeve, the opposing projections of sleeve contact and force the barbs of the needle hub inwardly until the barbs disengage from the opposing apertures of the cylinder hub, and wherein upon disengagement of the barbs from the cylinder hub, the needle hub including the needle are moved by the spring through the passage of the cylinder hub to the first end of the cylinder hub adjacent the closed upper end of the housing, leaving the infusion device positioned on the skin of the patient.

13. A method for retracting a needle of a device used to introduce a cannula of a subcutaneous infusion device into a subcutaneous layer of skin of a patient, the method comprising:
   removing a cap from the device, the cap including a tamper-evident band, wherein the tamper-evident band remains coupled to a housing when the cap is removed from the housing;
   introducing a cannula of a subcutaneous infusion device into a subcutaneous layer of skin of a patient using a needle of a device;

upon the full insertion of the cannula by the device and the device reaching a trigger state, allowing projections within the device to move opposing barbs towards one another to release the needle from the housing; and automatically retracting the needle while leaving the infusion device positioned on the skin of the patient.

14. The method of claim 13, further comprising reapplying the cap after introduction of the cannula.

15. The method of claim 13, further comprising preloading the infusion device in the device prior to application of the cap.

16. The method of claim 13, wherein the step of introducing the cannula further comprises providing a member in the device to automatically introduce the cannula of the subcutaneous infusion device into the subcutaneous layer of skin of the patient using the needle.

17. The method of claim 13, further comprising preloading the subcutaneous infusion device into the device.

18. The method of claim 13, further comprising:
coupling the cap to the housing to create a sterile environment;
providing the tamper-evident band coupled to the cap by tabs;
coupling the tamper-evident band to the housing; and
uncoupling the cap from the housing so that the tabs are broken and the tamper-evident band remains coupled to the housing.

* * * * *